(12) United States Patent
Belanoff et al.

(10) Patent No.: US 11,590,135 B2
(45) Date of Patent: *Feb. 28, 2023

(54) FATTY LIVER DISEASE TREATMENT USING GLUCOCORTICOID AND MINERALOCORTICOID RECEPTOR ANTAGONISTS

(71) Applicant: Corcept Therapeutics, Inc., Menlo Park, CA (US)

(72) Inventors: Joseph K. Belanoff, Menlo Park, CA (US); Hazel Hunt, Storrington (GB); Onno C. Meijer, Leiden (NL); José van den Heuvel, Leiden (NL)

(73) Assignee: Corcept Therapeutics, Inc., Menlo Park, CA (US)

( * ) Notice: Subject to any disclaimer, the term of this patent is extended or adjusted under 35 U.S.C. 154(b) by 249 days.

This patent is subject to a terminal disclaimer.

(21) Appl. No.: 17/111,288

(22) Filed: Dec. 3, 2020

(65) Prior Publication Data

US 2021/0085682 A1 Mar. 25, 2021

Related U.S. Application Data

(63) Continuation of application No. 16/256,295, filed on Jan. 24, 2019, now Pat. No. 10,881,660, which is a continuation of application No. 14/883,369, filed on Oct. 14, 2015, now Pat. No. 10,238,659.

(60) Provisional application No. 62/092,041, filed on Dec. 15, 2014, provisional application No. 62/064,358, filed on Oct. 15, 2014.

(51) Int. Cl.
*A61K 31/513* (2006.01)
*A61P 1/16* (2006.01)

(52) U.S. Cl.
CPC .............. *A61K 31/513* (2013.01); *A61P 1/16* (2018.01)

(58) Field of Classification Search
CPC ................................ A61K 31/513; A61P 1/16
See application file for complete search history.

(56) References Cited

U.S. PATENT DOCUMENTS

| | | |
|---|---|---|
| 2,153,546 A | 4/1939 | Camp et al. |
| 7,745,657 B2 | 6/2010 | Ali et al. |
| 8,685,973 B2 | 4/2014 | Clark et al. |
| 8,716,327 B2 | 5/2014 | Zhao et al. |
| 8,906,917 B2 | 12/2014 | Clark et al. |
| 9,321,736 B2 | 4/2016 | Clark et al. |
| 9,447,089 B2 | 9/2016 | Desai et al. |
| 10,238,659 B2 | 3/2019 | Belanoff et al. |
| 10,881,660 B2 | 1/2021 | Belanoff et al. |
| 2007/0066557 A1 | 3/2007 | Monia et al. |
| 2009/0312246 A1 | 12/2009 | Baron et al. |
| 2010/0004326 A1 | 1/2010 | Veverka |
| 2010/0144764 A1 | 6/2010 | Huang et al. |
| 2010/0298282 A1 | 11/2010 | Roach et al. |
| 2013/0072486 A1 | 3/2013 | Clark et al. |
| 2016/0106749 A1 | 4/2016 | Belanoff et al. |

FOREIGN PATENT DOCUMENTS

| | | | |
|---|---|---|---|
| WO | 2003105838 A2 | 12/2003 | |
| WO | 2004009017 A2 | 1/2004 | |
| WO | 2011140228 A1 | 11/2011 | |
| WO | 2012129074 A1 | 9/2012 | |
| WO | WO-2012129074 A1 * | 9/2012 | ........... A61K 31/505 |

OTHER PUBLICATIONS

Albaugh et al., "Olanzapine Promotes Fat Accumulation in Male Rats by Decreasing Physical Activity, Repartitioning Energy and Increasing Adipose Tissue Lipogenesis while Impairing Lipolysis", Molecular Psychiatry, vol. 16, No. 5, May 2011, pp. 569-581.
Anstee et al., "Mouse Models in Non-alcoholic Fatty Liver Disease and Steatohepatitis Research", Int J Exp Pathol., vol. 87, No. 1, Feb. 2006, pp. 1-16.
Atucha et al., "A Mixed Glucocorticoid/mineralocorticoid Selective Modulator with Dominant Antagonism in the Male Rat Brain", Endocrinology, vol. 156, No. 11, Nov. 2015, pp. 1-10.
Belanoff et al., "Selective Glucocorticoid Receptor {Type II} Antagonists Prevent Weight Gain Caused by Olanzapine in Rats", European Journal of Pharmacology, vol. 655, Issue 1-3, Mar. 25, 2011, pp. 117-120.
Bugianesi et al., "Non-Alcoholic Fatty Liver Disease/Non-Alcoholic Steatohepatitis (NAFLD/NASH): Treatment", Best Practice & Research Clinical Gastroenterology, vol. 18, Issue 6, Dec. 2004, pp. 1105-1116.
Caprio et al., "Pivotal Role of The Mineralocorticoid Receptor in Corticosteroid-Induced Adipogenesis", The Faseb Journal, vol. 21, No. 9, Jul. 2007, pp. 2185-2194.
Cooper et al., "Effects of Olanzapine in Male Rats: Enhanced Adiposity in the Absence of Hyperphagia, Weight Gain or Metabolic Abnormalities", Journal of Psychopharmacology, vol. 21, No. 4, Jun. 2007, pp. 405-413.
EP15851238.4 , "Extended European Search Report", dated May 4, 2018, 8 pages.
Fernø et al., "Olanzapine Depot Exposure in Male Rats: Dose-dependent Lipogenic Effects without Concomitant Weight Gain", European Neuropsychopharmacology, vol. 25, No. 6, Jun. 2015, pp. 923-932.
Goossens et al., "Translational Aspects of Diet and Non-Alcoholic Fatty Liver Disease", Nutrients, vol. 9, No. 1077, 2017, pp. 1-9.
Hashimoto et al., "Mifepristone Promotes Adiponectin Production and Improves Insulin Sensitivity in a Mouse Model of Diet-Induced-Obesity", PLoS ONE, vol. 8, Issue 11, e79724, Nov. 2013, pp. 1-16.
Hebbard et al., "Animal Models of Nonalcoholic Fatty Liver Disease", Nature, vol. 8, Jan. 2011, pp. 34-44.

(Continued)

*Primary Examiner* — Jeffrey S Lundgren
*Assistant Examiner* — Ibrahim D Bori
(74) *Attorney, Agent, or Firm* — Kilpatrick Townsend & Stockton LLP

(57) ABSTRACT

The present invention provides treatment of fatty liver disease using a class of pyrimidinedione cyclohexyl compounds.

20 Claims, 3 Drawing Sheets

(56) References Cited

OTHER PUBLICATIONS

Henderson et al., "Glucose Metabolism in Patients with SchizophreniaTreated with Atypical Antipsychotic Agents", Arch Gen Psychiatry, vol. 62, No. 1, Jan. 2005, pp. 19-28.
Hunt et al., "Discovery of a Novel Non-Steroidal GR Antagonist with in Vivo Efficacy in the Olanzapine-Induced Weight Gain Model in the Rat", Bioorganic & Medicinal Chemistry Letters, vol. 22, No. 24, 2012, pp. 7376-7380.
Koorneef et al., "Selective Glucocorticoid Receptor Modulation Prevents and Reverses Nonalcoholic Fatty Liver Disease in Male Mice", Endocrinology, vol. 159, No. 12, Dec. 1, 2018, pp. 3925-3936.
Larter et al., "Animal Models of NASH: Getting both Pathology and Metabolic Context Right", J. of Gastroenterology and Hepatology, vol. 23, 2008, pp. 1635-1648.
Lau et al., "Animal Models of Non-Alcoholic Fatty Liver Disease", J. Pathology, vol. 241, Nov. 22, 2016, pp. 36-44.
Lemke et al., "The Glucocorticoid Receptor Controls Hepatic Dyslipidemia Through Hes1", Cell Metabolism, vol. 8, No. 3, Sep. 3, 2008, pp. 212-223.
Minet-Ringuet et al., "Long Term Treatment with Olanzapine Mixed with the Food in Male Rats Induces Body Fat Deposition with no Increase in Body Weight and no Thermogenic Alteration", Appetite, vol. 46, No. 3, May 2006, pp. 254-262.
PCT/US2015/055487, "International Search Report and Written Opinion", dated Feb. 12, 2016, 11 pages.
PCT/US2015/055487, "Invitation to Pay Add'l Fees and Partial Search Report", dated Dec. 1, 2015, 2 pages.
Ray et al., "Discovery and Optimization of Novel, Non-Steroidal Glucocorticoid Receptor Modulators", Bioorganic & Medicinal Chemistry Letters,vol. 17, No. 17, 2007, pp. 4901-4905.
SG11201703024V, "Written Opinion", dated Apr. 20, 2018, 7 pages.
Soliman et al., "Histological Evaluation of the Role of Atypical Antipsychotic Drugs in Inducing Non-Alcoholic Fatty Liver Disease in Adult Male Albino Rats (Light and Electron Microscopic Study)", Folia Biologica, vol. 59, No. 5, 2013, pp. 173-180.
Takahashi et al., "Animal Models of Nonalcoholic Fatty Liver Disease/Nonalcoholic Steatohepatitis", World J Gastroenterology, vol. 18, No. 19, May 21, 2012, pp. 2300-2308.
Van Der Zwaal et al., "Modelling Olanzapine-induced Weight Gain in Rats", Int J Neuropsychopharmacol, vol. 17, No. 1, Jan. 2014, pp. 169-186.
Van Herck et al., "Animal Models of Nonalcoholic Fatty Liver Disease—A Starter's Guide", Nutrients, vol. 9, No. 1072, 2017, pp. 1-13.
Wada et al., "Spironolactone Improves Glucose and Lipid Metabolism by Ameliorating Hepatic Steatosis and Inflammation and Suppressing Enhanced Gluconeogenesis Induced by High-Fat and High-Fructose Diet", Endocrinology, vol. 151, No. 5, May 2010, pp. 2040-2049.
Asensio et al., "Role of Glucocorticoids in the Physiopathology of Excessive Fat Deposition and Insulin Resistance", International Journal of Obesity, vol. 28, Dec. 13, 2004, pp. S45-S52.
Chinese Patent Application No. 202010597452.8, "Office Action", dated Sep. 27, 2022, 13 pages.
D'Souza et al., "Consumption of a High-Fat Diet Rapidly Exacerbates the Development of Fatty Liver Disease that Occurs with Chronically Elevated Glucocorticoids", American Journal of Physiology-Gastrointestinal and Liver Physiology, vol. 302, Jan. 19, 2012, pp. G850-G861.

\* cited by examiner

FATTY LIVER DISEASE TREATMENT USING GLUCOCORTICOID AND MINERALOCORTICOID RECEPTOR ANTAGONISTS

CROSS-REFERENCES TO RELATED APPLICATIONS

This application is a Continuation of U.S. patent application Ser. No. 16/256,295, filed Jan. 24, 2019, which is a Continuation of U.S. patent application Ser. No. 14/883,369, filed Oct. 14, 2015 (now U.S. Pat. No. 10,238,659, issued Mar. 26, 2019), which claims priority to U.S. Provisional Patent Application No. 62/092,041, filed Dec. 15, 2014, and U.S. Provisional Patent Application No. 62/064,358, filed Oct. 15, 2014, the disclosures of which are incorporated herein in their entireties for all purposes.

BACKGROUND OF THE INVENTION

Liver disorders can be categorized in different groups of diseases, such as alcohol-induced fatty liver disease (AFLD), nonalcoholic fatty liver disease (NAFLD), drug- or alcohol-related liver diseases, viral diseases, immune-mediated liver diseases, metabolic liver diseases, and complications associated with hepatic insufficiency and/or liver transplantation. Nonalcoholic fatty liver disease is a common hepatic disorder with histological features similar to those of alcohol-induced fatty liver disease, in individuals who consume little or no alcohol. Fatty liver disease is due to an abnormal retention of lipid (fats) within hepatocytes.

Effective treatments for AFLD and NAFLD remain insufficient. To date, no therapeutic drug treatment is established for such patients. There is a need for novel therapeutic options for managing fatty liver disease.

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these include the ligand binding domain, GR-beta is unable to bind the natural ligand, and is constitutively localized in the nucleus. The GR is also known as the GR II.

Cortisol and other glucocorticoids can also act on the mineralocorticoid receptor (MR), in which case they are referred to as mineralocorticoids or mineralocorticoid receptor antagonists (MRAs). The mineralocorticoid receptor primarily regulates the salt concentration in the body. The MR can have substantially equal affinity for mineralocorticoids and glucocorticoids.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

In addition to cortisol, the biological effects of other steroids can be modulated at the GR level using receptor modulators, such as agonists, partial agonists and antagonists. When administered to subjects in need thereof, steroids can provide both intended therapeutic effects, e.g., by stimulating glucocorticoid receptor transrepression, as well as negative side effects, e.g. by chronic glucocorticoid receptor transactivation.

What is needed in the art are new compositions and methods for modulating GR receptors to treat fatty liver disease. Surprisingly, the present invention meets these and other needs.

BRIEF SUMMARY OF THE INVENTION

In one embodiment, the present invention provides a method of treating fatty liver disease. The method includes administering to a subject in need thereof, a therapeutically effective amount of a compound of Formula I, thereby treating the fatty liver disease, wherein the compound of Formula I has the structure:

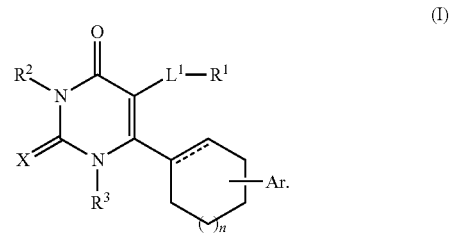

(I)

In the compound of Formula I, the dashed line is absent or a bond. X is O or S. $R^1$ is cycloalkyl, heterocycloalkyl, aryl or heteroaryl, optionally substituted with from 1 to 3 $R^{1a}$ groups. Each $R^{1a}$ is independently H, $C_{1-6}$ alkyl, $C_{2-6}$ alkenyl, $C_{2-6}$ alkynyl, $C_{1-6}$ alkoxy, $C_{1-6}$ alkyl-$OR^{1b}$, halogen, $C_{1-6}$ haloalkyl, $C_{1-6}$ haloaloxy, $-OR^{1b}$, $-NR^{1b}R^{1c}$, $-C(O)R^{1b}$, $-C(O)OR^{1b}$, $-OC(O)R^{1b}$, $-C(O)NR^{1b}R^{1c}$, $-NR^{1b}C(O)R^{1c}$, $-SO_2R^{1b}$, $-SO_2NR^{1b}R^{1c}$, cycloalkyl, heterocycloalkyl, aryl or heteroaryl. $R^{1b}$ and $R^{1c}$ are each H or $C_{1-6}$ alkyl. $R^2$ is H, $C_{1-6}$ alkyl, $C_{1-6}$ alkyl-$OR^{1b}$, $C_{1-6}$ alkyl-$NR^{1b}R^{1c}$ or $C_{1-6}$ alkylene-heterocycloalkyl. $R^3$ is H or $C_{1-6}$ alkyl. Ar is aryl, optionally substituted with 1-4 $R^4$ groups. Each $R^4$ is H, $C_{1-6}$ alkyl, $C_{1-6}$ alkoxy, halogen, $C_{1-6}$ haloalkyl or $C_{1-6}$ haloaloxy. $L^1$ is a bond or $C_{1-6}$ alkylene. Subscript n is an integer from 0 to 3. Also included are the salts and isomers of the compounds recited herein.

relative to control mice that received a high fat diet and vehicle. * p<0.05 "Compound 1" compared to "CTRL"

Figure 4:
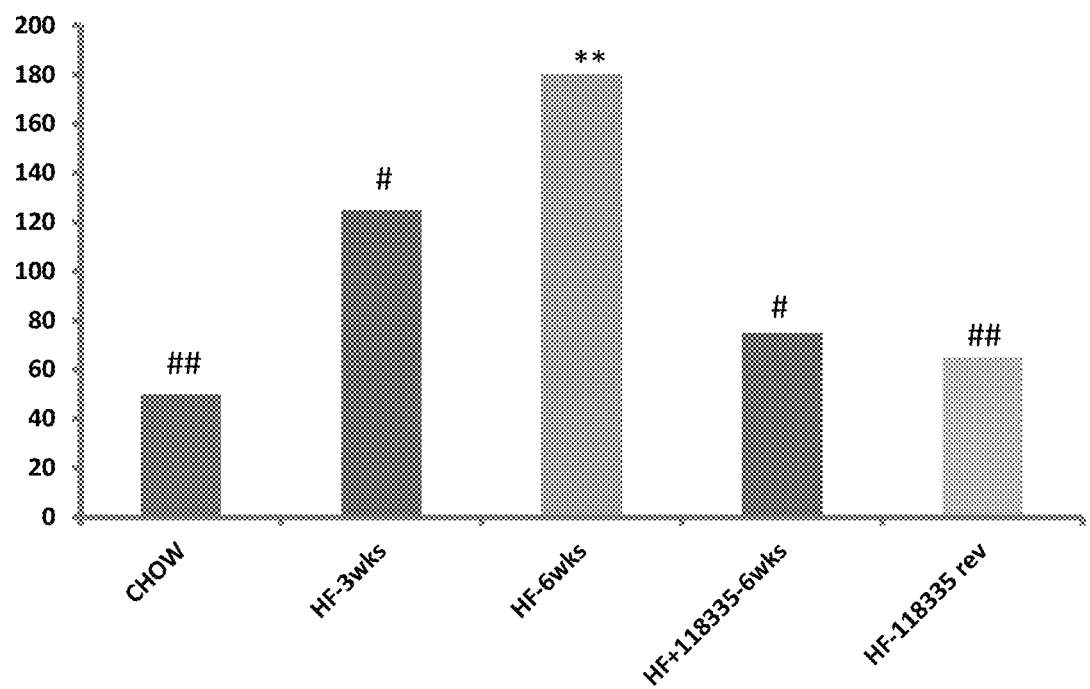

FIG. 4 shows triglyceride levels in livers of mice given a normal diet (the "CHOW" group), mice given a high fat diet for 3 weeks (the "HF-3wks" group), mice given a high fat diet for 6 weeks (the "HF-6wks" group), mice given a high fat diet and Compound 1 for 6 weeks (the "HF+118335-6wks" group), and mice given a high fat diet for 6 weeks with administration of Compound 1 only for the last 3 weeks (the "HF-118335 rev" group). ** p<0.01 compared to "CHOW"; #p<0.05 compared to "HF-6wks"; ##p<0.01 compared to "HF-6wks".

DETAILED DESCRIPTION OF THE INVENTION

I. General

The present invention provides compounds and methods for the treatment of fatty liver disease by administering a compound of the present invention to a patient suffering from a fatty liver disease. Without being bound by any theory, contrary to the accepted understanding in the art that the compounds of the present invention bind specifically to the glucocorticoid receptor, treatment of fatty liver disease in the present invention is accomplished by binding to both the glucorticoid and mineralocorticoid receptors, rather than binding specifically to the glucocorticoid receptor over other nuclear receptors such as the mineralocorticoid receptor and the progesterone receptor.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. For example, C$_1$-C$_6$ alkyl includes, but is not limited to, methyl, ethyl, propyl, butyl, pentyl, hexyl, iso-propyl, iso-butyl, sec-butyl, tert-butyl, etc.

"Alkylene" refers to either a straight chain or branched alkylene of 1 to 7 carbon atoms, i.e. a divalent hydrocarbon radical of 1 to 7 carbon atoms; for instance, straight chain alkylene being the bivalent radical of Formula —(CH$_2$)$_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain monosubstituted by C$_1$-C$_3$-alkyl (preferably methyl) or disubstituted on the same or different carbon atoms by C$_1$-C$_3$-alkyl (preferably methyl), the total number of carbon atoms being up to and including 7. One of skill in the art will appreciate that a single carbon of the alkylene can be divalent, such as in —CH((CH$_2$)$_n$CH$_3$)—, wherein n=0-5.

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatriynyl. Alkenyl groups can also have from 2 to 3, 2 to 4, 2 to 5, 3 to 4, 3 to 5, 3 to 6, 4 to 5, 4 to 6 and 5 to 6 carbons. The alkenyl groups is typically monovalent, but can be divalent, such as when the alkenyl group links two moieties together.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl groups is typically monovalent, but can be divalent, such as when the alkynyl group links two moieties together.

"Alkoxy" refers to an alkyl radical as described above which also bears an oxygen substituent capable of covalent attachment to another hydrocarbon for example, methoxy, ethoxy or t-butoxy group.

"Halogen," by itself or as part of another substituent, means, unless otherwise stated, a fluorine, chlorine, bromine, or iodine atom.

"Haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluoromethane refers to 1,1,1-trifluoromethyl.

"Haloalkoxy" refers to alkoxy as defined above where some or all of the hydrogen atoms are substituted with halogen atoms. "Haloalkoxy" is meant to include monohaloalkyl(oxy) and polyhaloalkyl(oxy).

"Alkylamine" refers to an alkyl groups as defined within, having one or more amino groups. The amino groups can be primary, secondary or tertiary. The alkyl amine can be further substituted with a hydroxy group. Alkyl amines useful in the present invention include, but are not limited to, ethyl amine, propyl amine, isopropyl amine, ethylene diamine and ethanolamine.

The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Cycloalkyl" refers to a saturated or partially unsaturated, monocyclic, fused bicyclic or bridged polycyclic ring assembly containing from 3 to 12 ring atoms, or the number of atoms indicated. For example, C$_3$-C$_8$ cycloalkyl includes cyclopropyl, cyclobutyl, cyclopentyl, cyclohexyl, cycloheptyl, and cyclooctyl. Cycloalkyl also includes norbornyl and adamantyl.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Alkylene-heterocycloalkyl" refers to a heterocycloalkyl group, as defined above, which is linked to another group by an alkylene. The heterocycloalkyl and the group to which the heterocycloalkyl is linked by an alkylene can be linked to the same atom or different atom of the alkylene.

"Aryl" means, unless otherwise stated, a polyunsaturated, aromatic, hydrocarbon substituent which can be a single ring or multiple rings (preferably from 1 to 3 rings) which are fused together or linked covalently. Examples include, but are not limited to, phenyl, biphenyl, naphthyl, and benzyl.

"Heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Likewise, the term "heteroarylalkyl" is meant to include those radicals in which a heteroaryl group is attached to an alkyl group.

Each of the above terms (e.g., "alkyl," "aryl" and "heteroaryl") are meant to include both substituted and unsubstituted forms of the indicated radical. Examples of substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NR(SO$_2$)R', —CN and —NO$_2$ in a number ranging from zero to (2 m'+1), where m' is the total number of carbon atoms in such radical. R', R", R"' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the present invention includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NR(SO$_2$)R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the present invention includes more than one R group, for example, each of the R groups is independently selected as are each R', R", R"' and R"" groups when more than one of these groups is present.

Where two substituents are "optionally joined together to form a ring," the two substituents are covalently bonded together with the atom or atoms to which the two substituents are joined to form a substituted or unsubstituted aryl, a substituted or unsubstituted heteroaryl, a substituted or unsubstituted cycloalkyl, or a substituted or unsubstituted heterocycloalkyl ring.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Hydrate" refers to a compound that is complexed to at least one water molecule. The compounds of the present invention can be complexed with from 1 to 10 water molecules.

"Isomers" refers to compounds with the same chemical formula but which are structurally distinguishable.

"Tautomer" refers to one of two or more structural isomers which exist in equilibrium and which are readily converted from one form to another.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Nuclear receptors" refers to a class of proteins responsible for sensing and responding to steroid and thyroid hormones, as well as synthetic hormones and compounds. There are a number of sub-families, including thyroid hormone receptor-like, retinoid X receptor-like, estrogen receptor-like, and nerve growth factor IB-like, among others. The subfamily estrogen receptor-like includes the families estrogen receptor, estrogen related receptor, and 3-ketosteroid receptors. The 3-ketosteroid receptors family includes numerous receptors such as, but not limited to, the glucocorticoid receptor (GR), the mineralocorticoid receptor (MR), the estrogen receptor (ER), the progesterone receptor (PR), and the androgen receptor (AR).

"Glucocorticoid receptor" ("GR") refers to a family of intracellular receptors which specifically bind to cortisol and/or cortisol analogs. The glucocorticoid receptor is also referred to as the cortisol receptor. The term includes isoforms of GR, recombinant GR and mutated GR. "Glucocorticoid receptor" ("GR") refers to the type II GR which specifically binds to cortisol and/or cortisol analogs such as dexamethasone (See, e.g., Turner & Muller, J Mol Endocrinol Oct. 1, 2005 35 283-292). Inhibition constants ($K_i$) for the compounds of the present invention against the human nuclear receptors are between 0.0001 nM to 1,000 nM; preferably between 0.0005 nM to 10 nM, and most preferably between 0.001 nM to 1 nM.

"Modulating a nuclear receptor" refers to methods for adjusting the response of a glucocorticoid receptor towards glucocorticoids, glucocorticoid antagonists, agonists, and partial agonists, as well as a mineralocorticoid receptor towards mineralocorticoids, MR antagonists, agonists and partial agonists. The methods include contacting a GR and MR with an effective amount of either an antagonist, an agonist, or a partial agonist and detecting a change in GR activity, or GR and MR activity.

"Nuclear receptor modulator" refers to any composition or compound which modulates the binding of a glucocorticoid receptor (GR) agonist, such as cortisol, or cortisol analogs, synthetic or natural, to a GR, as well as modulating the binding of a MR agonist, such as aldosterone, or analogs thereof, to a MR. The modulation can include partially or completely inhibiting (antagonizing) the binding of a GR agonist to a GR, and/or a MR agonist to a MR.

"Antagonizing" refers to blocking the binding of an agonist at a receptor molecule or to inhibiting the signal produced by a receptor-agonist. A receptor antagonist blocks or dampens agonist-mediated responses.

"Glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR.

"Specific glucocorticoid receptor antagonist" or "specific mineralocorticoid receptor antagonist" refers to any composition or compound which inhibits any biological response associated with the binding of a GR and/or an MR to an agonist. By "specific," we intend the drug to preferentially bind to the GR and/or MR rather than other nuclear receptors, such as the estrogen receptor (ER), progesterone receptor (PR) or the androgen receptor (AR).

"Mineralocorticoid receptor" refers to a family of intracellular receptors that bind to mineralocorticoids such as aldosterone, and glucocorticoids such as cortisol, with substantially equal affinity. The mineralocorticoid receptor (MR) is also referred to as the aldosterone receptor or nuclear receptor subfamily 3, group C, member 2, (NR3C2). The MR belongs to the cytosolic receptor family. The MR is activated by mineralocorticoids such as aldosterone and its precursor deoxycorticosterone as well as glucocorticoids, like cortisol.

"Mineralocorticoid receptor antagonist" refers to any composition or compound which partially or completely inhibits (antagonizes) the binding of a mineralocorticoid receptor (MR) agonist, such as aldosterone, or aldosterone analogs, synthetic or natural, to a MR.

"Patient" or "subject" refers to a living organism suffering from or prone to a condition that can be treated by administration of a pharmaceutical composition as provided herein. Non-limiting examples include humans, other mammals and other non-mammalian animals.

"Therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

The terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

"Fatty liver disease" refers to a disease or a pathological condition caused by, at least in part, abnormal hepatic lipid deposits. Fatty liver disease includes, e.g., alcoholic fatty liver disease, nonalcoholic fatty liver disease, and acute fatty liver of pregnancy. Fatty liver disease may be, e.g., macrovesicular steatosis or microvesicular steatosis.

"Alcohol-related liver disease" or "ARLD" refers to diseases of the liver that are wholly, or in part, caused by, or attributable to, excessive consumption of alcohol. There are four main types of ARLD, alcoholic fatty liver (AFL, a sub-type of fatty liver disease), alcoholic steatohepatitis (ASH), alcoholic-induced cirrhosis, and alcoholic hepatocellular cancer. As used herein, "excessive consumption of alcohol" generally refers to the consumption of more than about 15-30 g/day of ethanol.

The physiological effects of alcohol consumption on liver function or disease are dependent on a variety of genetic and non-genetic factors that modify both individual susceptibility and the clinical course of ARLD. Thus, in certain patients, ARLD can develop at much lower rates of alcohol consumption, including consumption of at least about 12 g/day, 15 g/day, 20 g/day, 25 g/day or more. Moreover, it is understood that in some patients, estimates of daily consumption of alcohol are an average value that includes periods of heavy alcohol consumption and periods of little or no alcohol consumption. Such an average value can include an average of alcohol consumption over at least about a week, two weeks, a month, three months, six months, nine months, a year, 2, 3, or 4 years, or more. In some cases, the determination of whether a liver dysfunction is an ARLD is based on reference to a variety of factors including, but not limited to: the amount and type of alcoholic beverage consumption (e.g., beer or spirits); the duration of alcohol abuse; patterns of drinking behavior (e.g., binge drinking, drinking without co-consumption of food, etc.); gender; ethnicity; co-existing disease conditions such as metabolic syndrome or diabetes, iron overload, or infection with hepatitis virus, genetic markers; family history; liver enzyme levels; proinflammatory cytokine levels; gene or protein expression analysis; or histopathological examination of liver tissue or cells.

"Liver disorder unrelated to excessive ingestion of alcohol" is a liver disorder that is distinguished from ARLD. Such a disorder therefore refers to a wide array of liver diseases that are not caused by alcohol consumption. For example, hepatitis can be caused by viral infection. A liver disorder caused by excessive alcohol consumption and other factors, is considered an ARLD rather than a liver disorder unrelated to excessive ingestion of alcohol. In contrast, a liver disorder merely exacerbated by excessive alcohol consumption is considered a liver disorder unrelated to excessive ingestion of alcohol.

"Nonalcoholic fatty liver disease" or "NAFLD" refers to a fatty liver disease characterized by the presence of fat (lipids) in the liver and no substantial inflammation or liver damage. NAFLD can progress into nonalcoholic steatohepatitis and then into irreversible, advanced liver scarring or cirrhosis.

"Nonalcoholic steatohepatitis" or "NASH" refers a fatty liver disease, which resembles alcoholic liver disease, but occurs in people who drink little or no alcohol. The major feature in NASH is fat in the liver, along with inflammation and damage. NASH can lead to cirrhosis, in which the liver is permanently damaged and scarred and is no longer able to function properly. A differential diagnosis of NASH versus NAFLD may be determined by liver biopsy.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Fatty Liver Disease

Fatty liver disease (FLD, also known as hepatosteatosis) is a prevalent liver condition that occurs when lipids accumulate in liver cells. The lipid accumulation causes cellular injury and makes the liver susceptible to further injuries. Fatty liver disease is characterized by the build-up of excessive fat (lipids) in liver cells, generally caused by abnormal retention of lipids by the liver cells (i.e., steatosis). In addition to fat, proteins and water are retained in the hepatocytes, which can lead to a ballooning of hepatocytes. The accumulation of fat in the liver may be attributed to a perturbation of one of the following steps in the lipid metabolism of hepatocytes and adipocytes: (1) increased free fatty acid delivery to the liver; (2) increased free fatty acid synthesis within the liver; (3) decreased beta-oxidation of fatty acids; and (4) decreased very low-density lipoprotein synthesis or secretion. (Bacon et al., Gastroenterology, 1994, 107:1103-1109).

FLD may arise from a number of sources, including excessive alcohol consumption and metabolic disorders, such as those associated with insulin resistance, obesity, and hypertension. The disease is most prevalent in individuals who are obese or who have diabetes. In alcohol induced fatty liver disease (AFL) initially fat accumulates in liver cells, but then the disease can progress to alcoholic hepatitis which causes the liver to swell and become damaged if the individual continues to consume alcohol. The individual can also develop alcoholic cirrhosis, or scarring of the liver which in turn can cause liver failure. Heavy drinkers can progress from AFL to alcoholic hepatitis to alcoholic cirrhosis over time.

Nonalcoholic fatty liver disease (NAFLD) is a liver disorder with histological features of AFL but in individuals who consume little to no alcohol. Like AFL, NAFLD is due to the abnormal retention of fat (lipids) by hepatocytes. Other fatty liver diseases can develop in a patient with other types of liver diseases, such as but not limited to, chronic viral hepatitis C (HCV), chronic viral hepatitis B (HBV), chronic autoimmune hepatitis (AIH), diabetes and Wilson's disease. Fatty liver can also be associated with indications caused by disruptions in lipid metabolism, such as disorders due to drugs, e.g., gastrointestinal disorders (e.g., intestinal bacterial outgrowth, gastroparesis and irritable bowel syndrome), chemotherapy, gastrointestinal surgeries for obesity, malnutrition and genetic defects in proteins that process lipids.

In some embodiments, the fatty liver disease is alcohol related liver disease (ARLD) or nonalcoholic fatty liver disease (NAFLD). In some instances, the alcohol related liver disease is alcohol fatty liver disease (AFL), alcoholic steatohepatitis (ASH) or alcoholic cirrhosis. In some instances, the nonalcoholic fatty liver disease is nonalcoholic steatohepatitis (NASH) or nonalcoholic cirrhosis.

A. Alcohol Related Liver Disease (ARLD)

Alcohol-related liver disease (ARLD) describes a family of alcohol-related, or alcohol-induced, liver pathologies including alcohol induced fatty liver disease (AFL), alcoholic hepatitis, and alcoholic cirrhosis. Virtually all persons who are chronic and heavy consumers of alcohol will develop AFL. Additionally, due to the high prevalence of complicating factors such as obesity, diabetes, and metabolic syndrome in the general population, many individuals who do not satisfy the criteria for chronic heavy consumers of alcohol are susceptible to developing AFL.

AFL can be diagnosed via ultrasound. Typically, the liver of a patient with AFL presents as "echogenic," meaning more dense than usual to the imaging sound waves. In addition, the liver is typically enlarged due to the swelling and presence of large amounts of fat.

AFL can also be indicated by, and thus diagnosed due to, presentation of one or more symptoms or risk factors (e.g., obesity, diabetes, drinking behavior, etc.). Fatty liver disease can present symptoms such as fatigue, muscle weakness, abdominal discomfort, weight loss, and confusion. However, fatty liver disease usually does not present overt physical symptoms. Fatty liver disease can also be accompanied by, or precede, inflammation of the liver or hepatic fibrosis. Patients with fatty liver disease generally present elevated serum liver enzyme levels. Moreover, the relative levels of several liver enzymes are altered. AFL generally presents with a serum aspartate aminotransferase (AST) level that is greater than the level of alanine aminotransferase (ALT). This is distinguished from non-alcoholic fatty liver disease, in which ALT is higher than AST.

There are four main pathogenic factors for AFL: (1) Increased generation of NADH caused by alcohol oxidation, favoring fatty acid and tri-glyceride synthesis, and inhibiting mitochondrial β-oxidation of fatty acids. (2) Enhanced hepatic influx of free fatty acids from adipose tissue and of chylomicrons from the intestinal mucosa. (3) Ethanol-mediated inhibition of adenosine monophosphate activated kinase (AMPK) activity resulting in increased lipogenesis and decreased lipolysis by inhibiting peroxisome proliferating-activated receptor α (PPARα) and stimulating sterol regulatory element binding protein 1c (SREBP1c). And, (4) Damage to mitochondria and microtubules by acetaldehyde, which results in a reduction of NADH oxidation and the accumulation of VLDL, respectively.

Successful treatment of AFL is indicated by improvement of one or more clinical, laboratory, or histopathological symptoms. For example, successful treatment can be indicated by a reduction in volume of fatty liver, e.g., as exhibited by ultrasound examination. As another example, successful treatment can be indicated by a reduction of one or more clinical symptoms such as fatigue, weakness, or cessation of weight loss. As another example, successful treatment can be indicated by a normalization of liver enzyme levels or relative levels (e.g., normalization of the aspartate aminotransferase/alanine aminotransferase ratio).

Alcoholic hepatitis, or alcoholic steatohepatitis (ASH), is the next stage of ARLD after AFL. As such, AFL is a pre-requisite for development of ASH. Seventeen percent of all liver biopsies of patients who are admitted for alcohol detoxification reveal ASH and 40% of patients with alcoholic cirrhosis also have ASH in a cirrhotic liver. Twenty-five percent of patients develop excessive liver necrosis with clinical signs of hepatic failure and hepatic encephalopathy. In severe cases ASH may cause profound liver damage, increased resistance to blood flow and is associated with a poor prognosis. Acute mortality of severe ASH is between about 15% and 25%. ASH is characterized by an inflammation of the liver. Various factors may contribute to the development of ASH, including: (1) acetaldehyde-induced toxic effects; (2) reactive oxygen species (ROS) generation and the resulting lipid peroxidation; (3) upregulation of proinflammatory cytokines; and (4) impaired ubiquitin-proteasome pathway function.

Acetaldehyde binds to proteins and to DNA resulting in functional alterations and protein adducts. Such adducts can activate the immune system by forming autoantigens. Acetaldehyde also induces mitochondria damage and impairs glutathione function, leading to oxidative stress and apoptosis.

The main sources of ROS are CYP2E1-dependent mitochondrial electron transport, NADH-dependent cytochrome reductase, and xanthine oxidase. Chronic alcohol intake markedly up-regulates CYP2E1, which exacerbates ROS generation. Moreover, CYP2E1 metabolizes ethanol to acetaldehyde resulting in further alteration of protein and DNA.

Alcohol metabolites and ROS stimulate signaling pathways such as those mediated by NF-κB, STAT-JAK, and JNK in hepatic resident cells, leading to the local synthesis of inflammatory mediators such as TNFα and CXC chemokines (e.g., interleukin-8), as well as osteopontin. Alcohol abuse also results in changes in the colonic microbiota and increased intestinal permeability, leading to elevated serum levels of lipopolysaccharides that induce inflammatory actions in Kupffer cells via CD14/TLR4. The resulting inflammatory milieu in the alcoholic liver leads to polymorphonuclear leukocyte (PMN) infiltration, ROS formation and hepatocellular damage.

ASH histopathology can be characterized by ballooning degeneration of hepatocytes associated with necrosis, enhanced apoptosis, and frequently, the occurrence of Mallory Denk bodies (MDBs). ASH histopathology can also exhibit infiltration of immune cells, including polymorphonuclear cells, T-lymphocytes, or natural killer cells. MDBs are associated with poor prognosis. In addition to MDB, giant mitochondria can be observed in the liver cells of patients with ASH. Additional histopathological characteristics of ASH include macrovesicular steatosis, microvesicular steatosis, lobular hepatitis, nuclear vacuoles, ductular proliferation, perivencular fibrosis, and fibrosis or cirrhosis.

Patients with ASH may develop progressive fibrosis. In ARLD, the fibrotic tissue is typically located in pericentral and perisinusoidal areas. In advanced stages, collagen bands are evident and bridging fibrosis develops. This condition precedes the development of regeneration nodules and liver cirrhosis. The cellular and molecular mechanisms of fibrosis in ARLD are not completely understood. Alcohol metabolites such as acetaldehyde can directly activate hepatic stellate cells (HSC), the main collagen-producing cells in the injured liver. HSC can also be activated paracrinally by damaged hepatocytes, activated Kupffer cells and infiltrating PMN cells. These cells release fibrogenic mediators such as growth factors (TGF-β1, PDGF), cytokines (leptin, angiotensin II, interleukin-8, and TNFα), soluble mediators (nitric oxide), and ROS. Importantly, ROS stimulate pro-fibrogenic intracellular signaling pathways in HSC including those mediated by ERK, PI3K/AKT, and JNK. They also up-regulate TIMP-1 and decrease the actions of metalloproteinases, thereby promoting collagen accumulation. Cells other than HSC can also synthesize collagen in ARLD. They include portal fibroblasts and bone-marrow derived cells.

ASH can be classified into mild, moderate, and severe forms due to the intensity and frequency of a wide variety of subjective and objective clinical findings. Clinical symptoms of ASH include: nonspecific upper right quadrant pain, nausea, and emesis, frequently accompanied by fever and jaundice. Other symptoms include: fatigue, dry mouth and increased thirst, or bleeding from enlarged veins in the walls of the lower part of the esophagus. Other skin conditions indicative of ASH include: small red spider-like veins on the skin, very dark or pale skin, redness on the feet or hands, or itching. Patients with ASH may also present with symptoms of alcohol withdrawal and signs of malnutrition. Further clinical markers include hepatomegaly, ascites, anorexia, encephalopathy, splenomegaly, weight loss, pancreatitis, or gastrointestinal bleeding. In severe cases, patients can exhibit problems with thinking, memory, and mood, fainting or lightheadedness, or numbness in legs and feet.

Serum and blood markers of ASH include an increase in the activity of aspartate aminotransferase and alanine aminotransferase, accompanied by a higher level of aspartate aminotransferase over alanine aminotransferase. Typically, gamma glutamyl peptidase is also elevated in ASH patients. Elevated gamma glutamyl peptidase is generally considered due to enzyme induction by ethanol; however, aspartate aminotransferase and alanine aminotransferase levels are considered to be markers of liver cell damage. 40-80% of patients also present with elevated alkaline phosphatase activity levels. In severe ASH, beta and gamma globulin levels are elevated. In addition, ASH can present with elevated leukocyte count with toxic granulation and fever. Hematologic abnormalities for ASH include macrocytotic hyperchromic anemia and thrombocytosis. Severe ASH can also exhibit reduction in parameters indicative of primary liver function such as prothrombin time, serum bilirubin, or serum albumin. In some cases, ASH can be detected by the presence of urine bilirubin.

ASH is generally indistinguishable from AFL via ultrasound. However ultrasound can be useful to exclude extrahepatic cholestasis, which can present similar clinical symptoms (e.g., jaundice). If diagnosis cannot be established by examination of clinical markers, serum or blood markers, and ultrasound, a liver biopsy may be performed. Liver biopsy can also be helpful to determine the severity of the disease or to guide pharmacological intervention.

Successful treatment of ASH is indicated by improvement of one or more clinical, laboratory, or histopathological symptoms. For example, successful treatment can be indicated by a reduction in volume of fatty liver, e.g., as exhibited by ultrasound examination. As another example, successful treatment can be indicated by a reduction of one or more clinical symptoms such as fatigue, weakness, or cessation of weight loss. As another example, successful treatment can be indicated by a normalization of liver enzyme levels or relative levels (e.g., normalization of the aspartate aminotransferase/alanine aminotransferase ratio). As yet another example, successful treatment can be indicated by a reduction in beta and gamma globulin levels or alkaline phosphatase levels. As another example, restoration or improvement of parameters of primary liver function such as prothrombin time, serum or urine bilirubin, and serum albumin can indicate successful treatment. As yet one more example, successful treatment can be indicated by amelioration, or cessation, of one or more of hepatomegaly, ascites, anorexia, encephalopathy, splenomegaly, weight loss, pancreatitis, or gastrointestinal bleeding.

Alcoholic cirrhosis is a late stage of serious liver disease marked by inflammation, swelling, fibrosis, damaged cellular membranes, scarring, and necrosis. Between about 10% to about 20% of heavy drinkers will develop cirrhosis of the liver. Symptoms of cirrhosis include, but are not limited to, jaundice, liver enlargement, and pain and tenderness. Successful treatment can be indicated by any reduction in the rate of progression of liver function deterioration.

B. Non-Alcoholic Fatty Liver Disease (NAFLD)

NAFLD includes a spectrum of histological forms including hepatic steatosis, and non-alcoholic steatohepatitis (NASH), which is characterized by liver inflammation, steatosis, necrosis and fibrosis due to the disruption of liver cells. Conditions associated with NAFLD are varied, and include type 2 diabetes, obesity, dyslipidemia, metabolic syndrome, treatment with hepatotoxic drugs, toxins, infectious agents, or other exogenous causes. For instance, NAFLD may result from metabolic disorders such as, e.g., galactosemia, glycogen storage diseases, homocystinuria, and tyrosemia, as well as dietary conditions such as malnutrition, total parenteral nutrition, starvation, and overnutrition. In certain cases, NAFLD is associated with jejunal bypass surgery. Other causes include exposure to certain chemicals such as, e.g., hydrocarbon solvents, and certain medications, such as, e.g., amiodarone, estrogens (e.g., synthetic estrogens), tamoxifen, maleate, methotrexate, nucleoside analogs, and perhexiline. Acute fatty liver conditions can also arise during pregnancy.

NAFLD typically follows a benign, non-progressive clinical course, however, NASH is a potentially serious condition. As many as 25% of NASH patients may progress to advanced fibrosis, cirrhosis and experience complications of portal hypertension, liver failure and hepatocellular carcinoma (Yeh and Brunt, *Am J Clin Pathol,* 2007, 128(5):837-47).

Individuals with NAFLD may be asymptomatic but clinical lab tests can show elevated liver enzyme levels. Individuals may exhibit symptoms of NAFLD, such as abdominal discomfort (e.g., discomfort in the right upper abdominal quadrant), acanthosis *nigricans*, bowel dismotility, coma, constipation, disseminated intravascular coagulopathy, epigastric pain, fatigue, malaise, hepatomegaly (generally with a smooth, firm surface upon palpation), hypoglycemia, jaundice, lipomatosis, lipoatrophy, lipodystrophy, nausea, neurological defects, Palmer erythema, panniculitis, periumbilical pain, small bowel bacterial overgrowth, spider angiomata, splenomegaly, subacute liver failure, and vomiting. Clinical evaluation to rule out alcohol related fatty liver disease may include determining if the individual consumes excess alcohol (e.g., >60 g/day for men and >20 g/day for women within the past 5 years. The presence or level of anti-hepatitis C antibody and serum ceruloplasmin levels can be used to indicate that the individual has NAFLD.

Non-invasive evaluation of biochemistry and metabolism can used to diagnose NAFLD and NASH. By using a biological sample such as blood, plasma or serum, high level of enzymes such as alanine aminotransferase (ALT), aspartate aminotransfersase (AST), alkaline Phosphatase (AP), and/or γ glutamyl transpeptidase (GGT), as well as the presence of other proteins of liver origin (including haptoglobin, total bilirubin, alpha-2-microglobulin, resistin, cleaved or intact cytokeratin-18) are commonly measured in addition to serum glucose and insulin resistance parameters. Since the level of ALT activity is frequently increased in NASH patients (Angulo and Lindor, *Best Pract Res Clin Gastroenterol,* 2002, 16(5):797-810), this criteria is considered as a surrogate marker for assessing liver injury.

In an individual suspected of having NAFLD or NASH, baseline testing of serum may include measuring or determining levels of AST, ALT, total and direct bilirubin, and fasting serum glucose, as well as a lipid panel. For example, steatosis may be indicated by elevated serum levels (often moderately elevated, e.g., elevated approximately 2, 3, 4, 5, 6, 7, 9, 10, 11, or 12-fold above normal levels) of liver enzymes (such as, e.g., AST, ALT, GGT and alkaline phosphatase) when other causes (such as, e.g., acute hepatitis, autoimmune disease, chronic hepatitis, cirrhosis, fulminant hepatitis, hepatocellular carcinoma, metastatic carcinoma, right heart failure, and viral hepatitis) have been eliminated. For example, ALT values greater than 32, 24, or 56 units per liter of serum or at least 2, 3, 4, 5, 6, 7, 8, 9, 10, 11, 12, or more times normal values may be indicative of a disorder associated with hepatic lipid deposits, or by AST values greater than 40 units per liter of serum or at least 2, 3, 4, 5, 6, 7, 8, 9, 10, 11, 12, or more times normal values. Mild to moderate elevation of serum aminotransferase levels is most commonly found (mean range, 100-200 IU/L). The ratio of AST/ALT is often less than one in NAFLD, but may be greater than one in patients with alcoholic liver disease or advanced liver disease or if the patient advances to fibrosis. GGT levels may also be significantly elevated, e.g., at least 2, 3, 4, 5, 6, 7, 8, 9, 10, 11, 12, or more times normal values as defined by a normal, healthy individual. Liver enzyme levels can be normal in a large percentage of patients with NAFLD, thus normal AST or ALT levels do not exclude the presence of advanced disease. Serum alkaline phosphatase and GGT levels may be mildly abnormal. Given that more than 80% of patients with NAFLD have some components of metabolic syndrome, serum levels of fasting cholesterol and triglycerides, as well as fasting glucose and insulin, may be determined. Albumin, bilirubin, and platelet levels may be normal unless the disease has evolved to cirrhosis. Some patients with NAFLD have low titers of autoimmune antibodies (e.g., antinuclear and anti-smooth muscle antibody) and an elevation of ferritin (Carey et al., "Nonalcoholic Fatty Liver Disease" in *Current Clinical Medicine*, 2$^{nd}$ edition, Elsevier, New York. In some embodiments, an AST/ALT ratio of greater than 1 can predict more advanced fatty liver disease.

Radiologic methods such as, but not limited to, x-ray imaging, ultrasonography, computed tomography (CT), magnetic resonance imaging (MRI), and magnetic resonance spectroscopy can be used to detect NAFLD. With ultrasonography, increased echogenicity of the liver compared to the kidneys can indicate liver steatosis.

NASH can be diagnosed using histopathological methods on liver samples (e.g., biopsies) to assess macrovesicular steatosis, ballooning degeneration, hepatocyte necrosis, lobular inflammation, megamitochondria, infiltration of inflammatory cells, apoptosis, and fibrosis (see, e.g., Brunt and Tiniakos, *World J Gastroenterol*, 2010, 16(42):5286-8296). Hepatocytic ballooning is characterized by swelling and enlargement of the cells, and sometimes the appearance of cytoplasmic alterations containing Mallory-Denk bodies. Fibrosis can also develop over time, initially as pericellular/pervenular fibrosis and eventually to portal-central bridging fibrosis and cirrhosis.

Hematoxylin and eosin (H&E), Masson trichrome, Oil Red O and immunohistochemical staining and other standard histological methods known to those of ordinary skill in the art can be performed to analyze tissue and cellular features. A scoring system (e.g., a NAFLD activity score) that includes one or more histological features can be used to score and diagnose NAFLD, including NASH. In some embodiments, the NASH Clinical Research Network Scoring System developed by the Pathology Committee of the NASH Clinical Research Network (see, e.g., Kleiner et al., *Hepatology*, 2005, 41(6): 1313-1321) can be used predict whether an individual has NAFLD or NASH. The Practice Guidelines published by the American Gastroenterological Association, American Association for the Study of Liver Diseases, and American College of Gastroenterology (Chalasani et al., *Gastroenterology*, 2012, 142: 1592-1609) can be followed by a clinician to diagnose or monitor NAFLD, including non-alcoholic fatty liver, NASH and NASH associated cirrhosis.

An individual's liver may be considered to be steatotic when a biopsy reveals at least 5-10% w/w fatty deposits (See, e.g., Clark et al., *J. Am. Med. Assoc.*, 2003, 289:3000-3004 (2003) and Adams et al., *Can. Med. Assoc.* 1, 2005, 172:899-905). A liver with fatty deposits comprising up to 25% (w/w) may be considered mildly steatotic, and a liver with fatty deposits comprising greater than 25% (w/w) may be considered severely steatotic.

Treatments for NAFLD including NASH include exercise, weight loss and avoiding hepatotoxins or any substance that may damage the liver. In some embodiments, therapies include administration of antioxidants, cytoprotective agents, antidiabetic agents, insulin-sensitizing agents (e.g. metformin), anti-hyperlipidemic agents, other chemical compounds, such as fibrates, thiazolidinediones (i.e., rosigli- tazone or pioglitazone), biguanidies, statins, cannabinoids, and other therapeutic compounds or molecules that target nuclear receptors, angiotensin receptors, cannabinoid receptors or HMG-CoA reductase.

Efficacy of treatment may be determined by detecting a reduction in one or more symptoms or clinical manifestations of a disease as well as any of the tests described above for diagnosis.

IV. Compounds

In some embodiments, the present invention provides a compound of formula I:

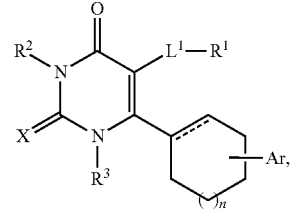

(I)

wherein the dashed line is absent or a bond. X is O or S. $R^1$ is cycloalkyl, heterocycloalkyl, aryl or heteroaryl, optionally substituted with from 1 to 3 $R^{1a}$ groups. Each $R^{1a}$ is independently H, $C_{1-6}$ alkyl, $C_{2-6}$ alkenyl, $C_{2-6}$ alkynyl, $C_{1-6}$ alkoxy, $C_{1-6}$ alkyl-$OR^{1b}$, halogen, $C_{1-6}$ haloalkyl, $C_{1-6}$ haloalkoxy, —$OR^{1b}$, —$NR^{1b}R^{1c}$, —$C(O)R^{1b}$, —$C(O)OR^{1b}$, —$OC(O)R^{1b}$, —$C(O)NR^{1b}R^{1c}$, —$NR^{1b}C(O)R^{1c}$, —$SO_2R^{1b}$, —$SO_2NR^{1b}R^{1c}$, cycloalkyl, heterocycloalkyl, aryl or heteroaryl. $R^{1b}$ and $R^{1c}$ are each H or $C_{1-6}$ alkyl. $R^2$ is H, $C_{1-6}$ alkyl, $C_{1-6}$ alkyl-$OR^{1b}$, $C_{1-6}$ alkyl-$NR^{1b}R^{1c}$ or $C_{1-6}$ alkylene-heterocycloalkyl. $R^3$ is H or $C_{1-6}$ alkyl. Ar is aryl, optionally substituted with 1-4 $R^4$ groups. Each $R^4$ is H, $C_{1-6}$ alkyl, $C_{1-6}$ alkoxy, halogen, $C_{1-6}$ haloalkyl or $C_{1-6}$ haloalkoxy. $L^1$ is a bond or $C_{1-6}$ alkylene. Subscript n is an integer from 0 to 3. Also included are the salts and isomers of the compounds recited herein.

In some other embodiments, the present invention provides a compound having formula Ia:

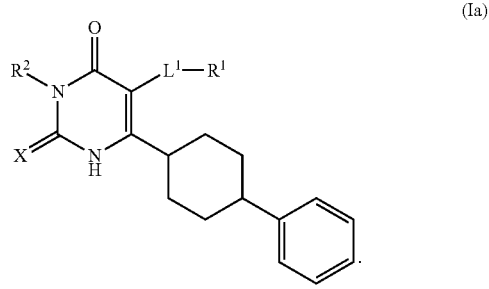

(Ia)

In some embodiments, $L^1$ is methylene. In other embodiments, Ar is phenyl.

In some embodiments, the present invention provides a compound having formula Ib:

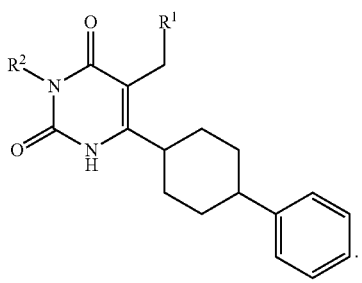

(Ib)

In some other embodiments, the present invention provides a compound having formula Ic:

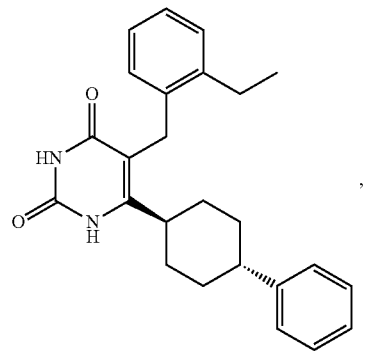

(Ic)

In some other embodiments, the present invention provides a compound having formula Id:

(Id)

In some embodiments, each $R^{1a}$, $R^2$ and $R^4$ are as defined above for Formula I. In some embodiments, the compounds of Formula Id are those where each $R^{1a}$ is independently H, $C_{1-6}$ alkyl, halogen, or $C_{1-6}$ haloalkyl; $R^2$ is H, or $C_{1-6}$ alkyl; and each $R^4$ is H, $C_{1-6}$ alkyl, halogen, or $C_{1-6}$ haloalkyl.

In some embodiments, the present invention provides a compound wherein $R^1$ is aryl or heteroaryl. In other embodiments, $R^1$ is selected from the group consisting of phenyl, pyridyl, pyrimidine, and thiazole. In some other embodiments, each $R^{1a}$ is independently H, $C_{1-6}$ alkyl, $C_{1-6}$ alkoxy, halogen, $C_{1-6}$ haloalkyl, —$NR^{1b}R^{1c}$, or —$SO_2R^{1b}$. In still other embodiments, each $R^{1a}$ is $C_{1-6}$ haloalkyl. In some other embodiments, each $R^{1a}$ is independently H, Me, Et, —OMe, F, Cl, —$CF_3$, —$NMe_2$, or —$SO_2Me$. In some embodiments, each $R^{1a}$ is independently H, Me, Et, F, Cl, or —$CF_3$. In other embodiments, each $R^{1a}$ is —$CF_3$. In some other embodiments, $R^2$ is H or $C_{1-6}$ alkyl. In other embodiments, $R^2$ is H.

In some embodiments, the present invention provides a compound selected from the following:

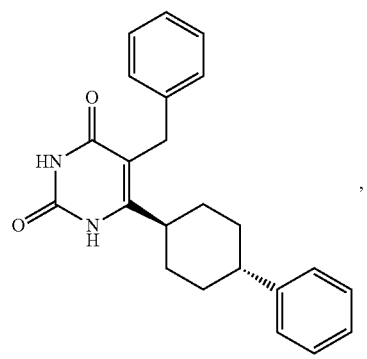

,

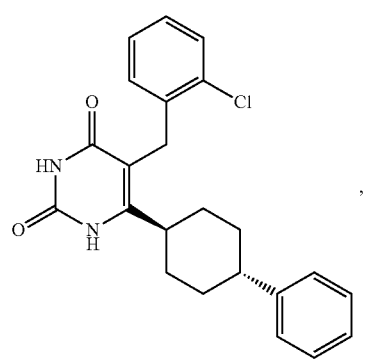

,

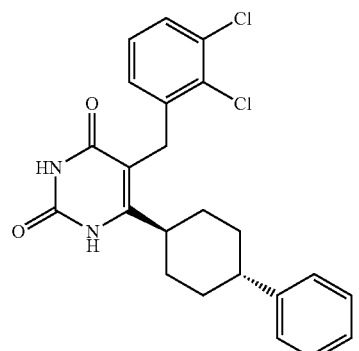

,

-continued
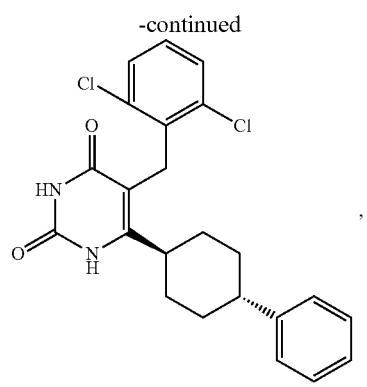
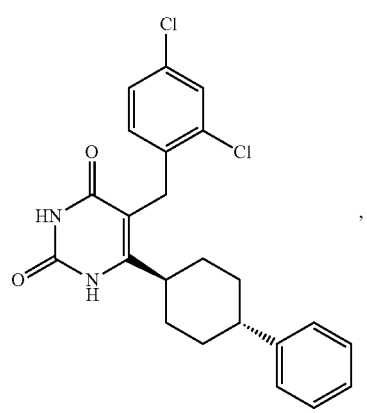
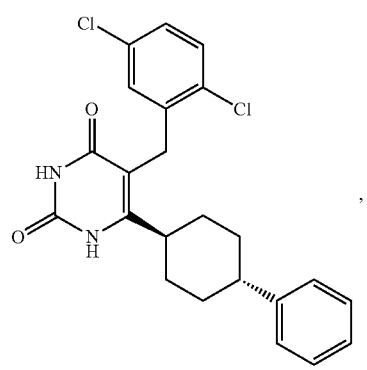
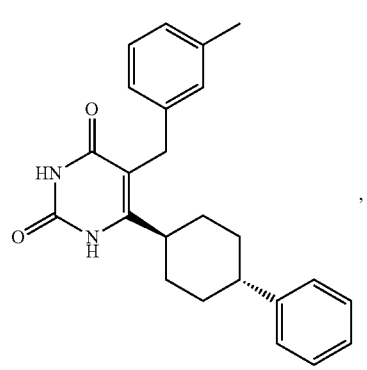
-continued
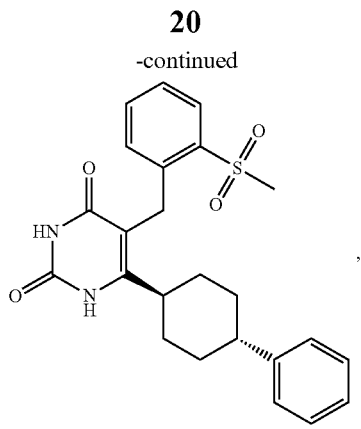
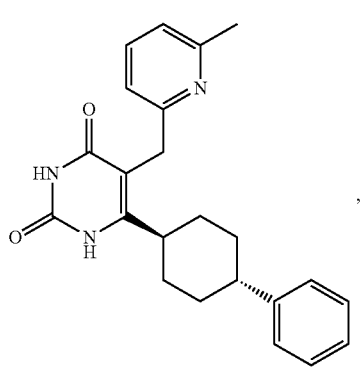
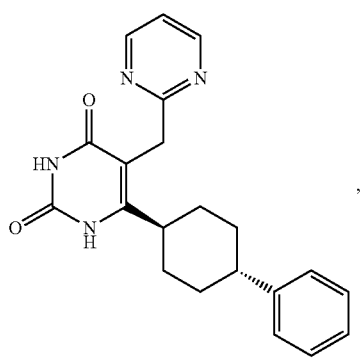
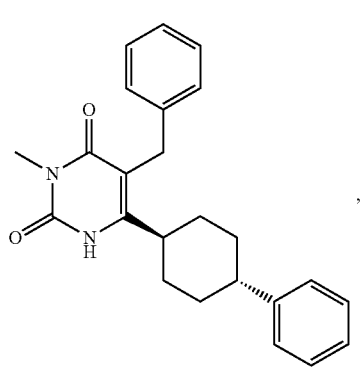

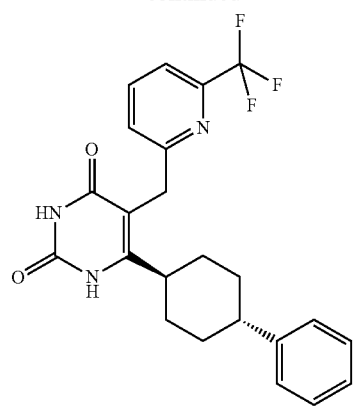
,
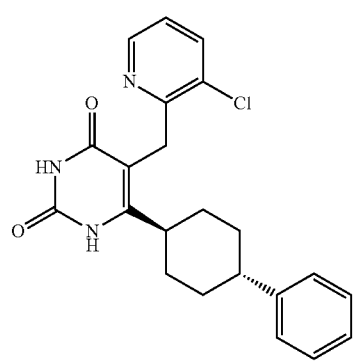
,
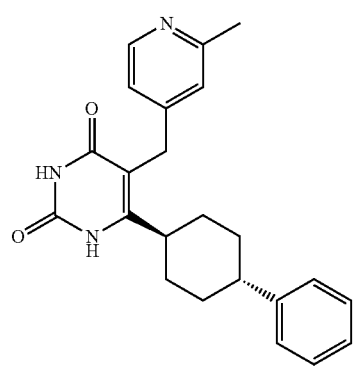
,
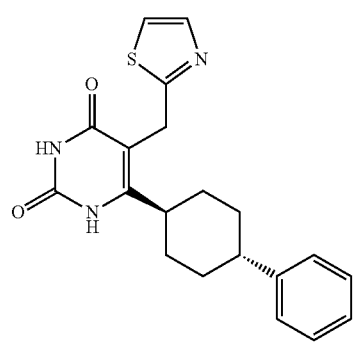
,
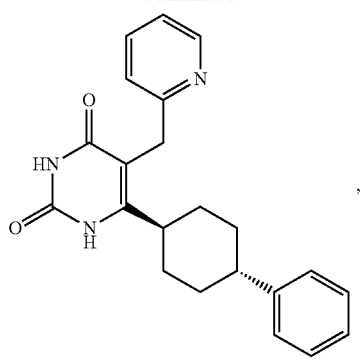
,
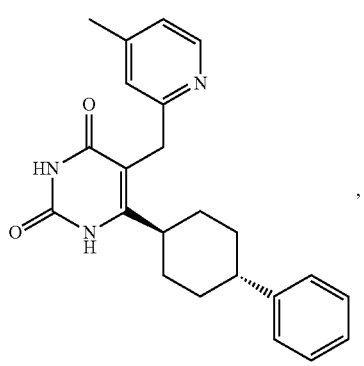
,
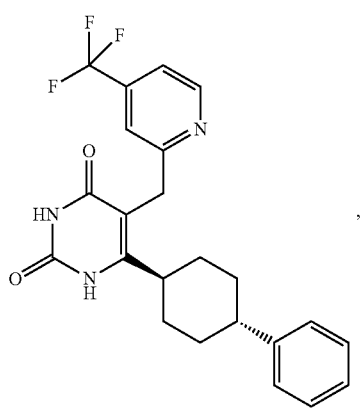
,
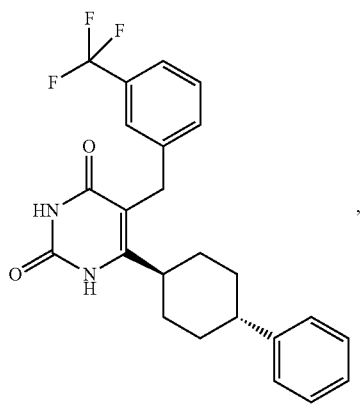
, 23
-continued
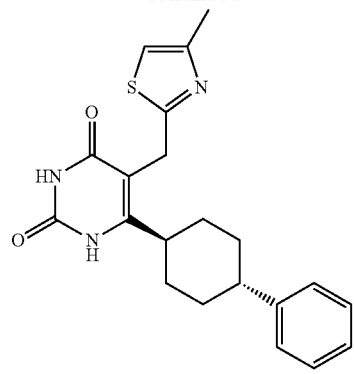
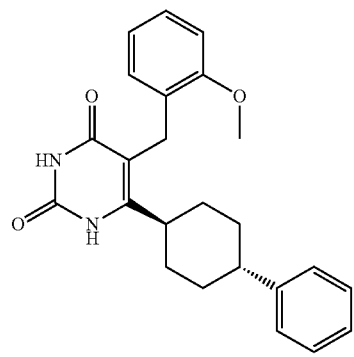
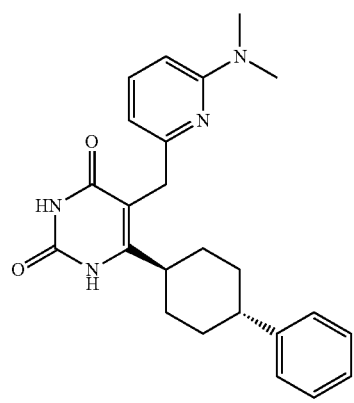
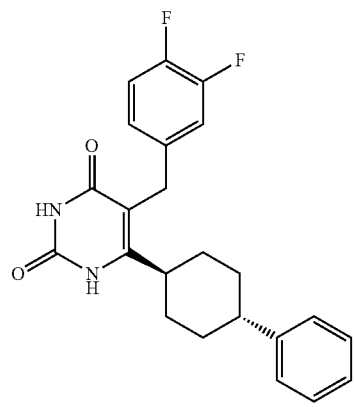
24
-continued
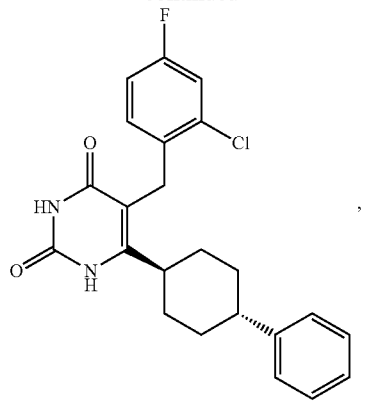
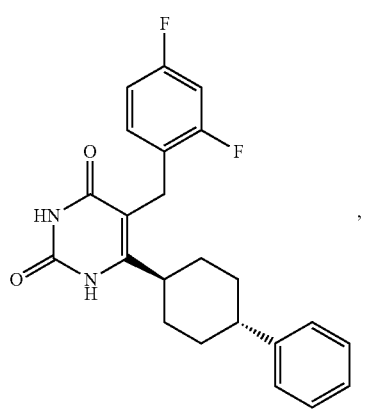
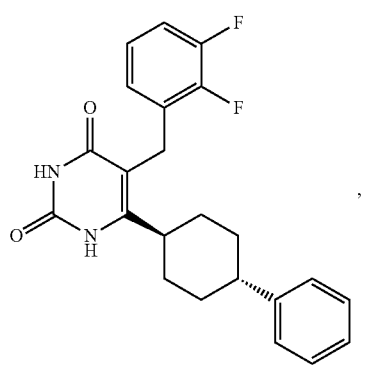
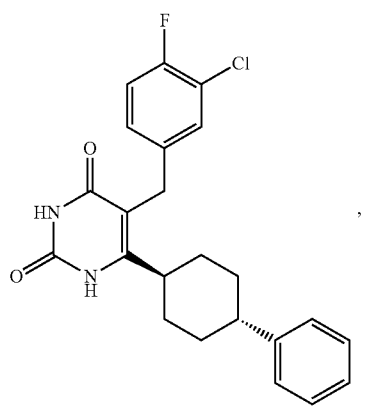

-continued
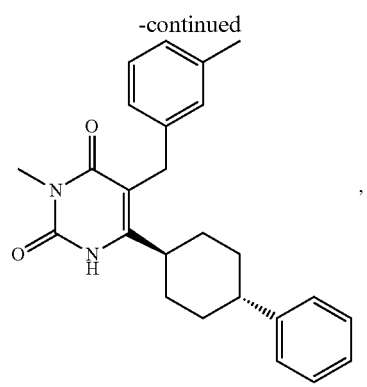
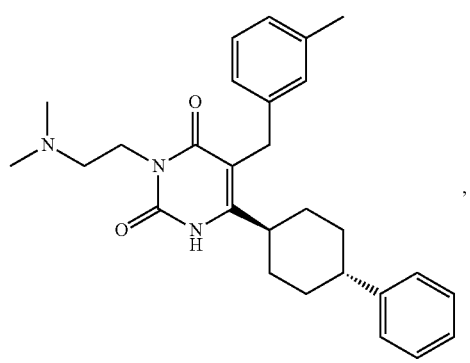
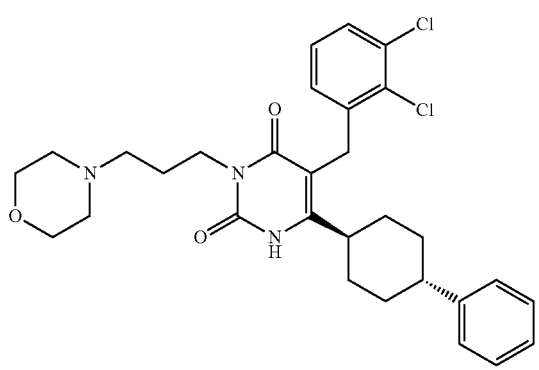
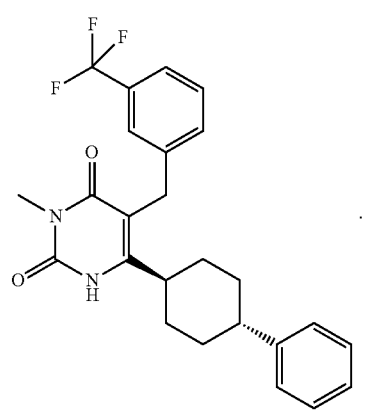
In some embodiments, the compound is
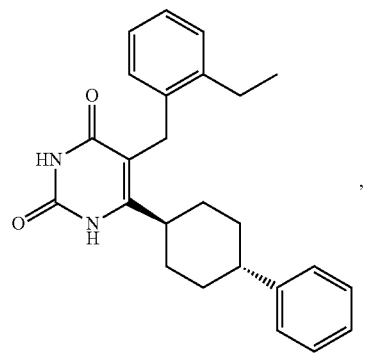
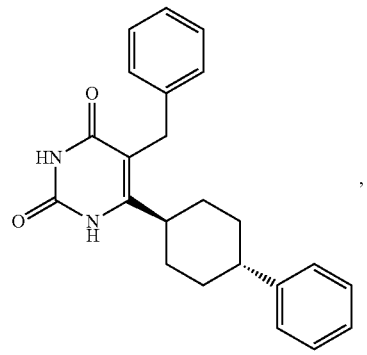
or
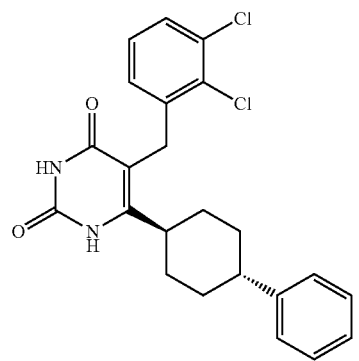

27
-continued
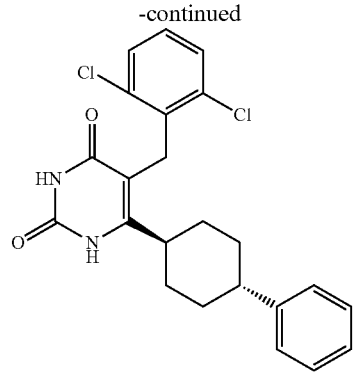
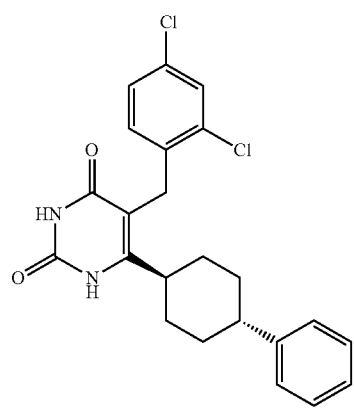
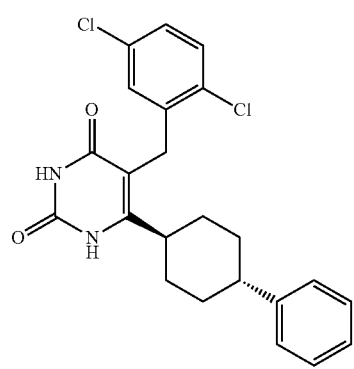
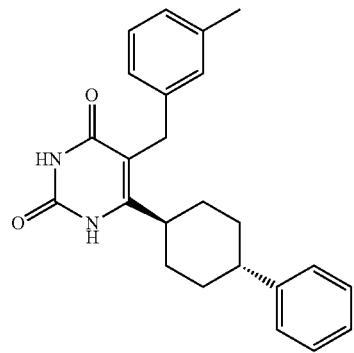
28
-continued
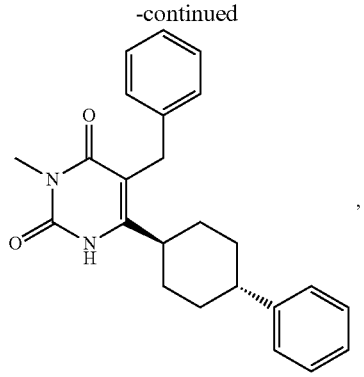
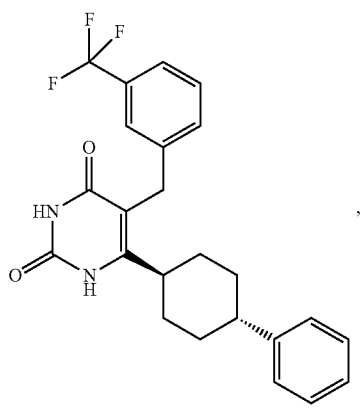
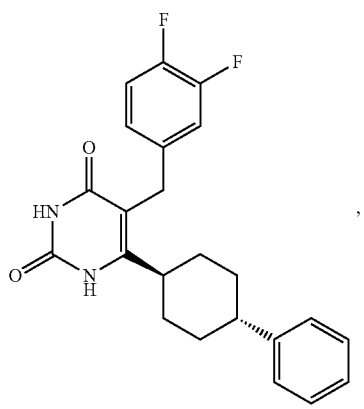
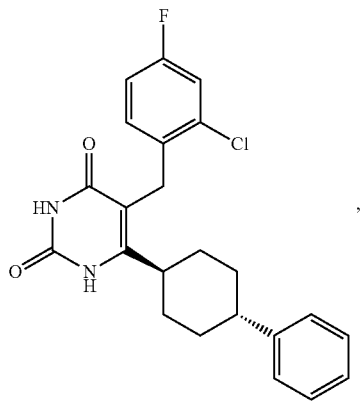

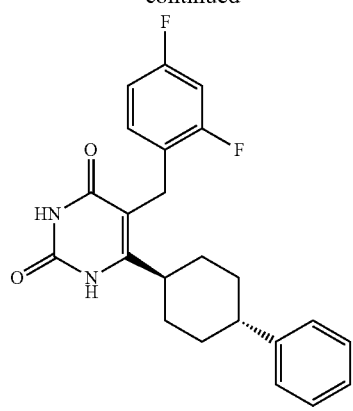

,

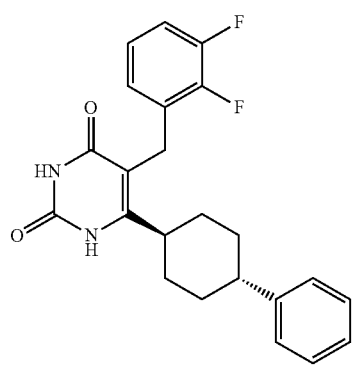

,

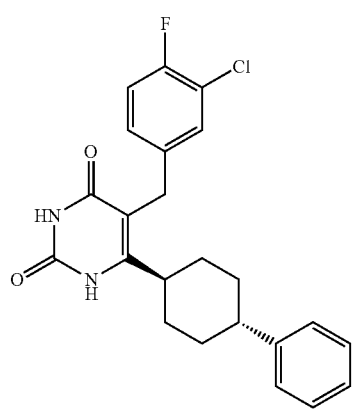

,

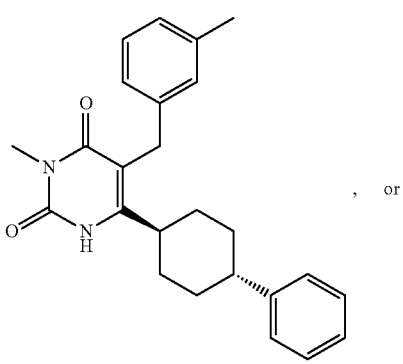

, or

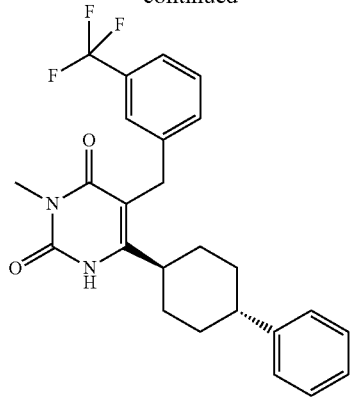

In some other embodiments, the present invention provides a compound having the formula:

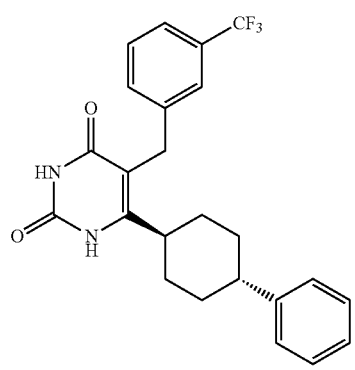

.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the present invention can be prepared by a variety of methods known in the art. See, for example, U.S. Pat. No. 8,685,973, herein incorporated by reference in its entirety.

V. Pharmaceutical Compositions

In some embodiments, the present invention provides a pharmaceutical composition including a pharmaceutically acceptable excipient and the compound of the present invention.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally.

Additionally, the compounds of the present invention can be administered transdermally. The GR modulators of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a compound of Formula (I), or a pharmaceutically acceptable salt of a compound of Formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound of the present invention in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds of the invention can be delivered by transdermally, by a topical route, formulated as applicator sticks, solutions, suspensions, emulsions, gels, creams, ointments, pastes, jellies, paints, powders, and aerosols.

The compounds and compositions of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) *J Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

Single or multiple administrations of formulations can be administered depending on the dosage and frequency as required and tolerated by the patient. The formulations should provide a sufficient quantity of active agent to effectively treat the disease state. Thus, in one embodiment, the pharmaceutical formulations for oral administration of the compound of the present invention is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

The compounds described herein can be used in combination with one another, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

After a pharmaceutical composition including a GR modulator of the invention has been formulated in an acceptable carrier, it can be placed in an appropriate container and labeled for treatment of an indicated condition. For administration of compounds of the present invention, such labeling would include, e.g., instructions concerning the amount, frequency and method of administration.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

VI. Method of Treating Fatty Liver Disease

In some embodiments, the present invention provides a method of treating a disorder or condition through modulating a glucocorticoid receptor, the method including administering to a subject in need of such treatment, a therapeutically effective amount of a compound of formula I.

In some other embodiments, the present invention provides a method of treating a disorder or condition through antagonizing a glucocorticoid receptor, the method including administering to a subject in need of such treatment, an effective amount of the compound of formula I.

In another embodiment, the present invention provides methods of modulating nuclear receptor activity using the techniques described herein. In an exemplary embodiment, the method includes contacting a GR and a MR with an effective amount of a compound of the present invention, such as the compound of formula I, and detecting a change in GR and MR activity.

In an exemplary embodiment, the nuclear modulator is an antagonist of GR and MR activity. A nuclear receptor antagonist, as used herein, refers to any composition or compound which partially or completely inhibits (antagonizes) the binding of a glucocorticoid receptor (GR) agonist (e.g. cortisol and synthetic or natural cortisol analog) to a GR, and partially or completely inhibits (antagonizes) the binding of a mineralocorticoid receptor (MR) agonist (e.g. aldosterone and synthetic or natural aldosterone analog) to a MR, thereby inhibiting any biological response associated with the binding of a GR and a MR to the agonist. In some embodiments, the nuclear receptor antagonist preferentially binds to the GR and/or MR over the estrogen receptor (ER), progesterone receptor (PR) and/or the androgen receptor (AR). The preference of the nuclear receptor antagonist for GR and/or MR over the ER, PR and/or AR can be greater than at least 10:1. For example, the preference can be at least 10:1, 50:1, 100:1, 500:1 or at least 1000:1. In some embodiments, the nuclear receptor antagonist preferentially binds to the GR and/or MR over the ER, PR and/or AR by at least 100:1.

In some embodiments, the nuclear receptor antagonist of the present invention can be used in combination with one or more treatments to ameliorate or reduce one or more symptoms of fatty liver disease. The nuclear antagonist can be administered to a patient with fatty liver disease who is undergoing or has undergone lifestyle modifications, such as, adoption of a weight loss regimen or caloric restriction, increased exercise, and/or avoidance of alcohol or heptatoxins. The patient may undergo or have undergone weight-reduction surgery (bariatric surgery). In some embodiments, the specific glucocorticoid receptor antagonist is administered to an individual in combination with a therapeutic agent, such as but not limited to, propylthiouracil, infliximab, insulin, glucagon, calcium channel blockers, antioxidants (e.g., vitamin E), S-adenosyl-L-methionine (SAMe), silymarin, and pentoxyfylline to treat alcoholic related fatty liver disease including AFL and ASH. In other embodiments, the specific glucocorticoid receptor antagonist is administered to an individual with a therapeutic agent, such as but not limited to, a serotonin reuptake inhibitor, sibutramine, orlistat, insulin-sensitizing agent (e.g., thiazolidinedione, rosiglitasone and pioglitazone), lipid-lowering agent (e.g., probucol), antioxidants (e.g., vitamin E, pentoxifylline, betaine and N-acetylcysteine), hepatoprotective therapy (e.g., ursodeoxycholic acid), angiotensin-converting enzyme inhibitor, angiotensin-receptor block, metformin, monounsaturated fatty acids, polyunsaturated fatty acids, and combinations thereof to treat nonalcoholic fatty liver disease including NASH.

VII. Assays and Methods for Testing Compounds to Treat Fatty Liver Disease

The compounds of the present invention can be tested for their antiglucocorticoid properties. Methods of assaying compounds capable of modulating glucocorticoid receptor activity are presented herein. Typically, compounds of the current invention are capable of modulating nuclear receptor activity by binding to the nuclera receptors such as GR and MR, or by preventing GR and MR ligands from binding to the corresponding GR and MR. In some embodiments, the compounds exhibit little or no cytotoxic effect.

A. Binding Assays

In some embodiments, nuclear receptor modulators are identified by screening for molecules that compete with a ligand of the nuclear receptor, such as dexamethasone. Those of skill in the art will recognize that there are a number of ways to perform competitive binding assays. In some embodiments, the nuclear receptor is pre-incubated with a labeled nuclear receptor ligand and then contacted with a test compound. This type of competitive binding assay may also be referred to herein as a binding displacement assay. Alteration (e.g., a decrease) of the quantity of ligand bound to the nuclear receptor indicates that the molecule is a potential nuclear receptor modulator. Alternatively, the binding of a test compound to the nuclear receptor can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical*

*Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a nuclear receptor ligand and the binding agent can be nuclear receptor bound to a solid phase. Alternatively, the labeled analyte can be labeled nuclear receptor and the binding agent can be a solid phase nuclear receptor ligand. The concentration of labeled analyte bound to the capture agent is inversely proportional to the ability of a test compound to compete in the binding assay.

Alternatively, the competitive binding assay may be conducted in liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the nuclear receptor may be altered by the binding of the nuclear receptor to its ligand or test compound. This alteration in the labeled nuclear receptor results in a decrease or increase in the signal emitted by label, so that measurement of the label at the end of the binding assay allows for detection or quantitation of the nuclear receptor in the bound state. A wide variety of labels may be used. The component may be labeled by any one of several methods. Useful radioactive labels include those incorporating $^3H$, $^{125}I$, $^{35}S$, $^{14}C$, or $^{32}P$. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art.

High-throughput screening methods may be used to assay a large number of potential modulator compounds. Such "compound libraries" are then screened in one or more assays, as described herein, to identify those library members (particular chemical species or subclasses) that display a desired characteristic activity. Preparation and screening of chemical libraries is well known to those of skill in the art. Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

B. Cell-Based Assays

Cell-based assays involve whole cells or cell fractions containing nuclear receptor to assay for binding or modulation of activity of nuclear receptor by a compound of the present invention. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, nuclear receptor can be expressed in cells that do not express an endogenous version of nuclear receptor.

In some cases, fragments of nuclear receptor, as well as protein fusions, can be used for screening. When molecules that compete for binding with nuclear receptor ligands are desired, the nuclear receptor fragments used are fragments capable of binding the ligands (e.g., dexamethasone). Alternatively, any fragment of nuclear receptor can be used as a target to identify molecules that bind nuclear receptor. nuclear receptor fragments can include any fragment of, e.g., at least 20, 30, 40, 50 amino acids up to a protein containing all but one amino acid of nuclear receptor. Typically, ligand-binding fragments will comprise transmembrane regions and/or most or all of the extracellular domains of nuclear receptor.

In some embodiments, signaling triggered by nuclear receptor activation is used to identify nuclear receptor modulators. Signaling activity of nuclear receptor can be determined in many ways. For example, downstream molecular events can be monitored to determine signaling activity. Downstream events include those activities or manifestations that occur as a result of stimulation of a nuclear receptor receptor. Exemplary downstream events useful in the functional evaluation of transcriptional activation and antagonism in unaltered cells include upregulation of a number of response element (RE)-dependent genes (PEPCK, tyrosine amino transferase, aromatase). In addition, specific cell types susceptible to nuclear receptor activation may be used, such as osteocalcin expression in osteoblasts which is downregulated by glucocorticoids; primary hepatocytes which exhibit nuclear receptor mediated upregulation of PEPCK and glucose-6-phospahte (G-6-Pase)). RE-mediated gene expression has also been demonstrated in transfected cell lines using well-known RE-regulated sequences (e.g. the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); or expression of genes regulated by NF-κB or AP-1 transcription factors in transfected cell-lines.

Typically, compounds that are tested in whole-cell assays are also tested in a cytotoxicity assay. Cytotoxicity assays are used to determine the extent to which a perceived modulating effect is due to non-nuclear receptor binding cellular effects. In an exemplary embodiment, the cytotoxicity assay includes contacting a constitutively active cell with the test compound. Any decrease in cellular activity indicates a cytotoxic effect.

C. Specificity

The compounds of the present invention may be subject to a specificity assay (also referred to herein as a selectivity assay). Typically, specificity assays include testing a compound that binds nuclear receptor in vitro or in a cell-based assay for the degree of binding to non-nuclear receptor proteins. Selectivity assays may be performed in vitro or in cell based systems, as described above. Nuclear receptor binding may be tested against any appropriate non-nuclear receptor protein, including antibodies, receptors, enzymes, and the like. In an exemplary embodiment, the non-nuclear receptor binding protein is a cell-surface receptor or nuclear receptor. In another exemplary embodiment, the non-nuclear receptor protein is a steroid receptor, such as estrogen receptor, progesterone receptor, or androgen receptor.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the nuclear receptor modulator compounds are equally applicable to the methods of treating disease states and/or the pharmaceutical compositions described herein. All publications, patents, and patent applications cited herein are hereby incorporated by reference in their entirety for all purposes.

VIII. Examples

Example 1. GR Reporter Gene Assay Using SW1353/MMTV-5 Cells

SW1353/MMTV-5 is an adherent human chondrosarcoma cell line that contains endogenous glucocorticoid receptors. It was transfected with a plasmid (pMAMneo-Luc) encoding firefly luciferase located behind a glucocorticoid-responsive element (GRE) derived from a viral promoter (long terminal repeat of mouse mammary tumor virus). A stable cell line SW1353/MMTV-5 was selected with geneticin, which was required to maintain this plasmid. This cell line was thus sensitive to glucocorticoids (dexamethasone) leading to expression of luciferase ($EC_{50}^{dex}$ 10 nM). This dexamethasone-induced response was gradually lost over time, and a new culture from an earlier passage was started (from a cryo-stored aliquot) every three months.

In order to test for a GR-antagonist, such as Compound 1, SW1353/MMTV-5 cells were incubated with several dilutions of the compounds in the presence of $5\times EC_{50}^{dex}$ (50 nM), and the inhibition of induced luciferase expression was measured using luminescence detected on a Topcount (Britelite Plus kit, Perking Elmer). For each assay, a dose-response curve for dexamethasone was prepared in order to determine the $EC_{50}^{dex}$ required for calculating the $K_i$ from the $IC_{50}$ of the test compound, e.g., Compound 1.

SW1353/MMTV-5 cells were distributed in 96-well plates and incubated in medium (without geneticin) for 24 hrs. Dilutions of the test compound in medium+50 nM dexamethasone were added and the plates further incubated for another 24 hours after which the luciferase expression is measured.

Compound 1 is named (E)-6-(4-phenylcyclohexyl)-5-(3-trifluoromethylbenzyl)-1H-pyrimidine-2,4-dione or 6-((1r,4r)-4-phenylcyclohexyl)-5-(3-(trifluoromethyl)benzyl)pyrimidine-2,4(1H,3H)-dione, and has the chemical structure shown below.

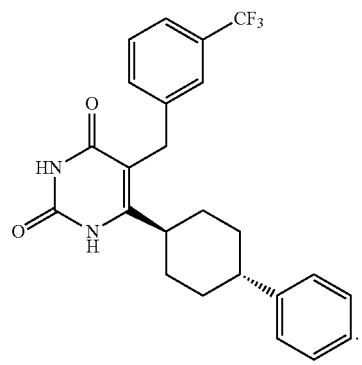 [SMILES: O=c1[nH]c(=O)c(Cc2cccc(C(F)(F)F)c2)c([C@H]2CC[C@H](c3ccccc3)CC2)[nH]1]

Compound 1 is an antagonist of the glucocorticoid receptor (GRII). In reporter gene assays, Compound 1 has a $K_i$ of 24 nM for GR.

Example 2. MR and PR Reporter Gene Assays Using T47D/MMTV-5 Cells

T47D/MMTV-5 is an adherent human breast carcinoma cell line containing endogenous mineralocorticoid and progesterone receptors (PR). As described for the SW1353 cell line above, T47D cells were transfected with the same pMAMneo-Luc plasmid, and stable lines were selected with geneticin. A cell line T47D/MMTV-5 was isolated, which responded to aldosterone ($EC_{50}$ 100 nM) and progesterone ($EC_{50}$ 10 nM), leading to expression of luciferase. To test for MR or PR antagonists, the T47D/MMTV-5 cells were incubated with several dilutions of the compounds in the presence of 5 times the $EC_{50}$ of the agonist aldosterone or progesterone. For each assay, a dose response curve was prepared for both aldostreone and progesterone.

T47D/MMTV-5 calls were distributed in 96-well plates (100 µl) in RPMI640 medium+10% charcoal stripped FCS. The cells were incubated for 24 hours in a $CO_2$ oven. A volume of 100 µl of the compound dilutions in medium+agonist (500 nM aldosterone, 50 nM progesterone) were added, and the plates were incubated for another 24 hours, after which luciferase expression was measured.

Compound 1 is an antagonist of the mineralocorticoid receptor (MR, GM). In reporter gene assays, Compound 1 has a $K_i$ of 148 nM for MR. Compound 1 is inactive in a progesterone receptor reporter gene assay.

Example 3. Determination of Liver Lipids in Mice Fed a High Fat Diet

Figure 1:
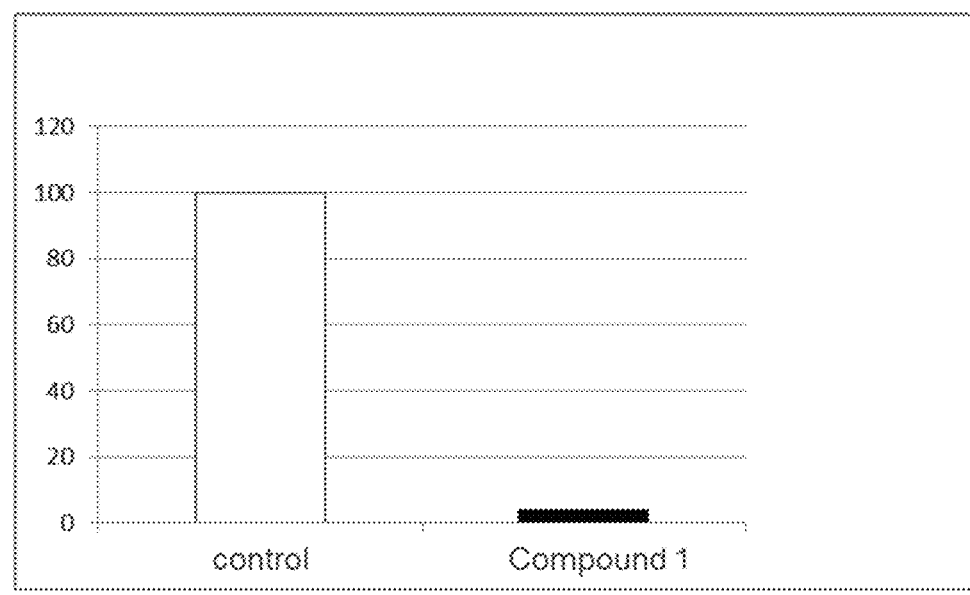
FIG. 1 shows the percentage of fat (lipid droplets) in Oil Red O stained livers from mice that received a high fat diet and Compound 1 (60 mg/kg/day) relative to control mice that received a high fat diet and vehicle.
Figure 2A:
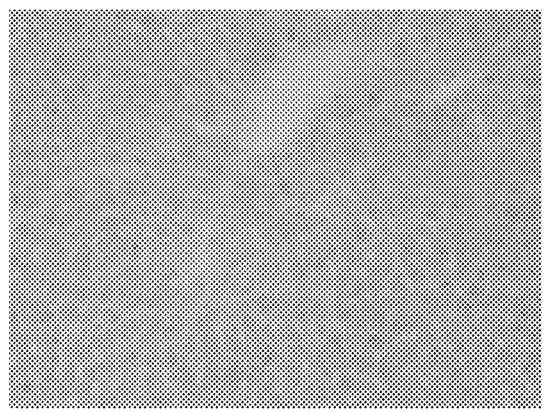
FIGS. 2A and 2B show Oil Red O staining of lipid droplets from livers from a mouse that received a high fat ("HF") diet and Compound 1 (FIG. 2A) and a control mouse that received a high fat diet and vehicle (FIG. 2B).
Figure 2B:
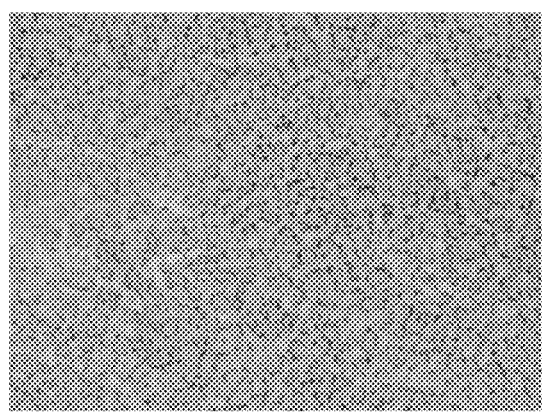
Figure 3:
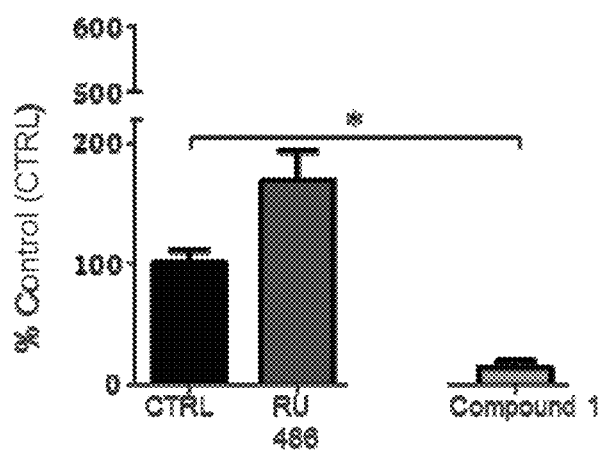
FIG. 3 shows the percentage of fat (lipid droplets) in Oil Red O stained livers from mice that received a high fat diet and either mifepristone or Compound 1 (60 mg/kg/day)

C57B16/J mice (n=8 per group) were given a high fat diet (60% fat) for three weeks and then sacrificed. Livers were collected and weighed. Liver slices were prepared and analysed for lipid levels by Oil Red O staining (FIGS. 1 and 3). One group of mice received Compound 1 mixed in the food (60 mg/kg/day) whilst another group of mice received vehicle mixed in the food. The livers of Compound 1 fed mice had no or low level of lipid droplets (FIG. 2A), while the control mice had more lipid droplets (FIG. 2B). An additional group received mifepristone (RU-486; 60 mg/kg/day) in the food. Compound 1 has GR antagonist activity and some MR antagonist activity. The data shows that mifepristone caused increased fatty liver compared to the controls. Compound 1 had an opposite effect and did not induce fatty liver.

In a separate experiment (FIG. 4), the accumulation of fat in the livers of mice fed a high fat diet (60% fat) and then sacrificed was determined by homogenizing the livers and extracting triglycerides. This experiment included 5 groups of mice:
Group 1 ("CHOW"): normal diet for 6 weeks;
Group 2 ("HF-3wks"): high fat diet for 3 weeks;
Group 3 ("HF-6wks"): high fat diet for 6 weeks;
Group 4 ("HF+118335-6wks"): high fat diet and Compound 1 for 6 weeks;
Group 5 ("HF-118335 rev"): high fat diet for 3 weeks followed by high fat diet and Compound 1 for 3 weeks.

Example 4. GR Protein:Protein Interaction Assay

Protein:protein interaction assays were used to determine the ability of test compounds to act as antagonists of the glucocorticoid receptor and/or mineralocorticoid receptor. These assays utilize a commercial assay platform provided by DiscoveRx Corp. (Fremont, Calif.). DiscoveRx technology is based on β-galactosidase enzyme fragment complementation using a luminogenic substrate. Briefly, Chinese hamster ovary cells (CHO-K1) have been engineered to express either human recombinant GR or MR together with a steroid responsive coactivator protein (SRCP) called PGC1α (peroxisome proliferator activated receptor gamma coactivator 1α). The assay measures the net outcome of GR or MR activation, i.e., nuclear translocation from the cytoplasm and interaction of the GR or MR with the coactivator PGC1α in the cell nucleus. The assay can be configured in both agonist and antagonist modes.

The cells (100 µl) were plated into 96 well plates and placed in a 37° C., 5% $CO_2$ incubator for 24 hours. After removing the cells from the incubator, 5 µl of test compound or vehicle was added to each well, and the plates were incubated for 1 hour at 37° C., 5% $CO_2$. Dexamethasone (5 µl of 792 nM solution) or vehicle was added to each well of the plates, and the plates were incubated for 6 hours at 37° C., 5% $CO_2$. The detection reagent was added, 55 µl per well, and the plates were incubated at room temperature in the dark without mixing. The plates were read for luminescence using an EnVision® plate reader (3 hour read). Luminescence values were expressed as a percent inhibition (% inhibition) of 36 nM dexamethasone, and $K_i$ values were calculated from the experimentally determined $IC_{50}$ values using the Cheng-Prusoff equation. It was determined that Compound 1 has a $K_i$ of 118 nM in this assay.

Example 5. MR Protein:Protein Interaction Assay

The cells (100 µl) were plated into 96 well plates and placed in a 37° C., 5% $CO_2$ incubator for 24 hours. After removing the cells from the incubator, 5 µl of test compound or vehicle was added to each well, and the plates were incubated for 1 hour at 37° C., 5% $CO_2$. Aldosterone (5 µl of 88 nM solution) or vehicle was added to each well of the plates, and the plates were incubated for 6 hours at 37° C., 5% $CO_2$. The detection reagent was added, 55 µl per well, and the plates were incubated at room temperature in the dark without mixing. The plates were read for luminescence using an EnVision® (Perkin Elmer, Walthan, Mass.) plate reader (3 hour read). Luminescence values were expressed as a percent inhibition (% inhibition) of 4 nM aldosterone, and $K_i$ values were calculated from the experimentally determined $IC_{50}$ values using the Cheng-Prusoff equation. It was determined that Compound 1 has a $K_i$ of 125 nM in this assay.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating fatty liver disease, comprising:
administering to a subject in need thereof, a therapeutically effective amount of a compound of Formula Id for said fatty liver disease, thereby treating the fatty liver disease,
wherein said administering comprises oral administration of said compound of Formula Id, wherein the compound of Formula Id has the structure:

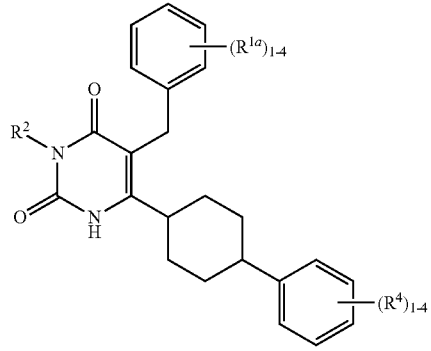

(Id)

wherein
each $R^{1a}$ is independently H, $C_{1-6}$ alkyl, halogen, or $C_{1-6}$ haloalkyl;
$R^2$ is H, or $C_{1-6}$ alkyl; and
each $R^4$ is H, $C_{1-6}$ alkyl, halogen, or $C_{1-6}$ haloalkyl;
or salts or isomers thereof.

2. The method of claim 1, wherein the fatty liver disease is alcohol related liver disease (ARLD) or -nonalcoholic fatty liver disease (NAFLD).

3. The method of claim 2, wherein the alcohol related liver disease is selected from alcohol fatty liver disease (AFL), alcoholic steatohepatitis (ASH) and alcoholic cirrhosis.

4. The method of claim 2, wherein the nonalcoholic fatty liver disease is selected from nonalcoholic steatohepatitis (NASH) and nonalcoholic cirrhosis.

5. The method of claim 1, wherein each $R^{1a}$ is $C_{1-6}$ haloalkyl.

6. The method of claim 1, wherein each $R^{1a}$ is independently selected from the group consisting of H, Me, Et, F, CL, or —$CF_3$.
7. The method of claim 1, wherein each $R^{1a}$ is —$CF_3$.
8. The method of claim 1, wherein $R^2$ is H.
9. The method of claim 1, wherein the compound of Formula Id is selected from the group consisting of:
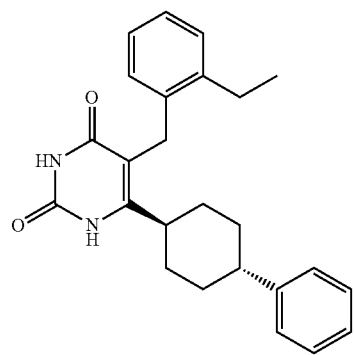
,
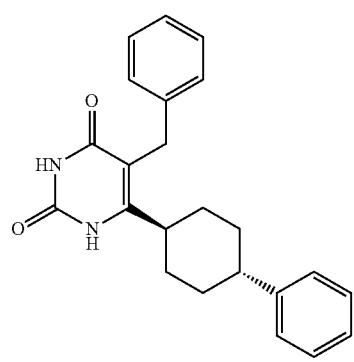
,
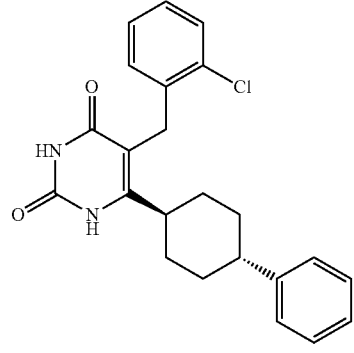
,
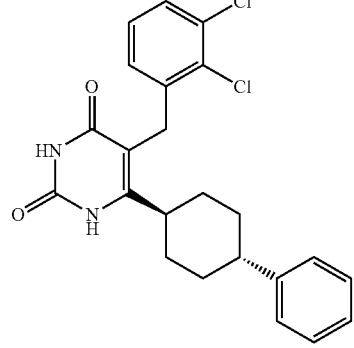
,
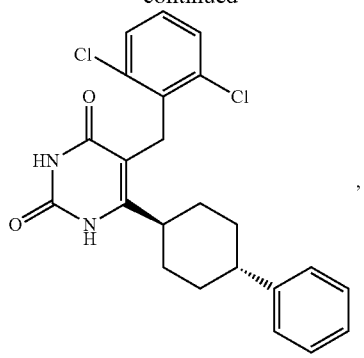
,
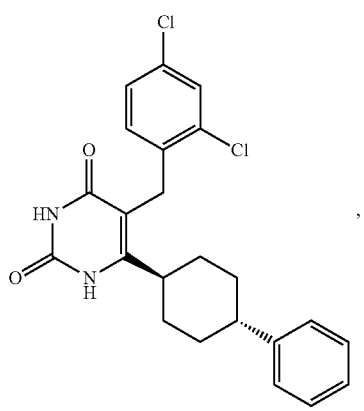
,
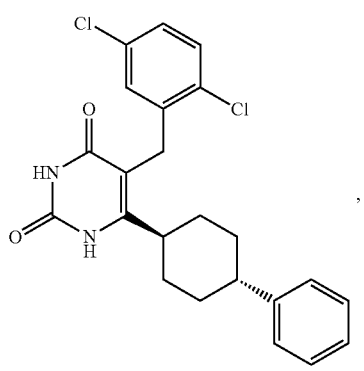
,
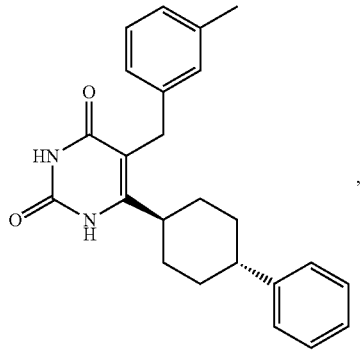
, 47
-continued
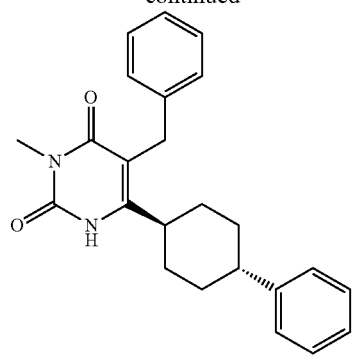
,
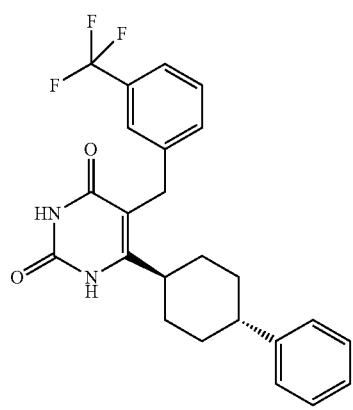
,
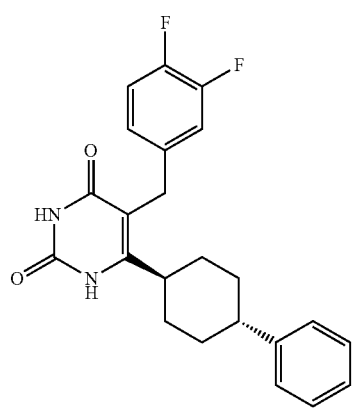
,
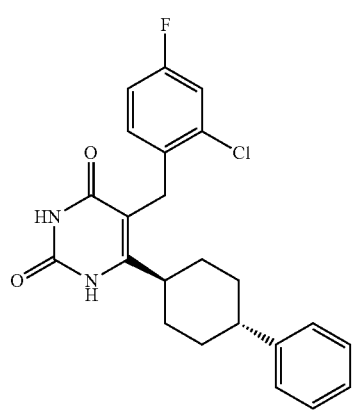
,
48
-continued
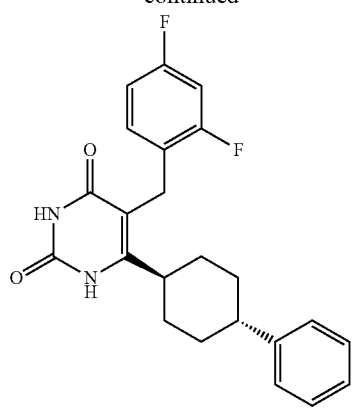
,
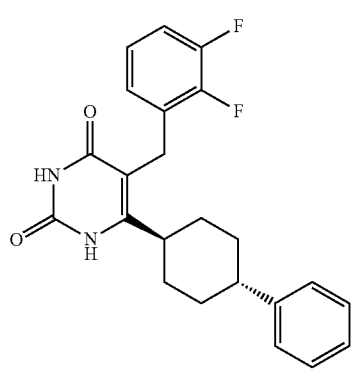
,
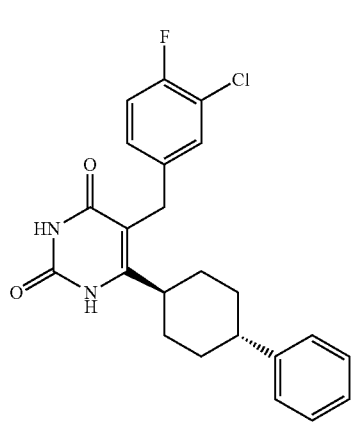
,
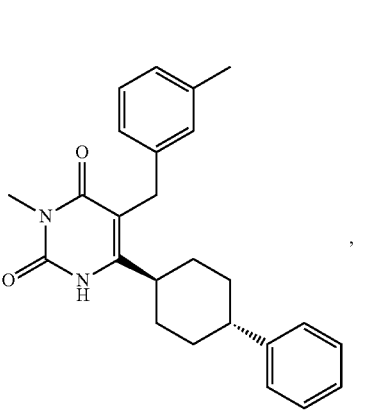
, and -continued

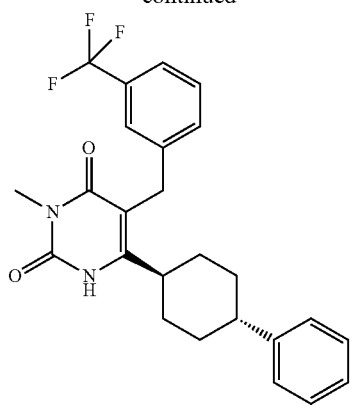

10. The method of claim 1, the compound of Formula Id having the formula:

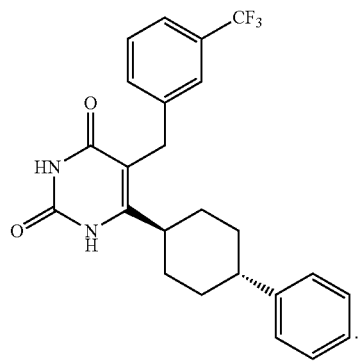

11. The method of claim 1, wherein said compound of Formula Id is an antagonist of the glucocorticoid receptor.

12. The method of claim 1, wherein said compound of Formula Id is an antagonist of the mineralocorticoid receptor.

13. The method of claim 1, wherein said compound of Formula Id inhibits glucocorticoid binding to the glucocorticoid receptor and is an antagonist of the mineralocorticoid receptor.

14. The method of claim 1, wherein said compound of Formula Id inhibits glucocorticoid binding to the glucocorticoid receptor with an inhibition constant ($K_i$) of between about 0.0001 nanomolar (nM) to 1000 nM and is an antagonist of the mineralocorticoid receptor.

15. The method of claim 13, wherein said fatty liver disease is an alcoholic-related fatty liver disease.

16. The method of claim 14, wherein said fatty liver disease is an alcoholic-related fatty liver disease.

17. The method of claim 13, wherein said fatty liver disease is a nonalcoholic fatty liver disease.

18. The method of claim 14, wherein said fatty liver disease is a nonalcoholic fatty liver disease.

19. The method of claim 17, wherein said nonalcoholic fatty liver disease is selected from nonalcoholic steatohepatitis (NASH) and nonalcoholic cirrhosis.

20. The method of claim 18, wherein said nonalcoholic fatty liver disease is selected from nonalcoholic steatohepatitis (NASH) and nonalcoholic cirrhosis.

\* \* \* \* \*